United States Patent [19]

Nagase et al.

[11] Patent Number: 5,939,551

[45] Date of Patent: Aug. 17, 1999

[54] PROCESS FOR PRODUCING 4A-ARYLDECAHYDROISOQUINOLINE DERIVATIVES

[75] Inventors: Hiroshi Nagase; Kuniaki Kawamura; Koji Ohshima; Koji Kawai, all of Kamakura, Japan

[73] Assignee: Toray Industries, Inc., Tokyo, Japan

[21] Appl. No.: 09/000,121

[22] PCT Filed: May 15, 1996

[86] PCT No.: PCT/JP96/01272

§ 371 Date: Apr. 6, 1998

§ 102(e) Date: Apr. 6, 1998

[87] PCT Pub. No.: WO97/43263

PCT Pub. Date: Nov. 20, 1997

[51] Int. Cl.$^6$ .................................................. C07D 217/04
[52] U.S. Cl. ............................................................ 546/144
[58] Field of Search ............................................. 546/144

[56] References Cited

U.S. PATENT DOCUMENTS 4,189,583  2/1980  Gless et al. .............................. 546/141

OTHER PUBLICATIONS

Bartmann et al., Synthetic Communications, vol. 18, No. 7, pp. 711–715, 1988.
Judd et al., Journal of Medicinal Chemistry, vol. 35, No. 1, pp. 48–56, Jan. 10, 1992.
Cantrell et al., J. Org. Chem., vol. 54, No. 6, pp. 1442–1445, 1989.

*Primary Examiner*—Zinna Northington Davis
*Attorney, Agent, or Firm*—Birch, Stewart Kolasch & Birch, LLP

[57] ABSTRACT

The present invention provides a novel process for producing 4a-aryldecahydroisoquinoline compounds. The process is especially useful for preparing 4a-trans-6-oxo-aryldecahydroisoquinoline compounds.

11 Claims, No Drawings

PROCESS FOR PRODUCING 4A-ARYLDECAHYDROISOQUINOLINE DERIVATIVES

This application is the national phase under 35 U.S.C. §371 of prior PCT International Application No., PCT/JP96/01272, which has an International filing date of May 15, 1996, which designated the United States of America, the entire contents of which are hereby incorporated by reference.

TECHNICAL FIELD

The present invention relates to a process for producing 4a-aryldecahydroisoquinoline derivatives. The 4a-aryldecahydroisoquinoline derivatives are useful as analgesics and/or narcotic antagonists as disclosed in Japanese Laid-open Patent Application (Kokai) No. 5-155857, and as materials for synthesizing immunosuppressive agents as disclosed in WO 839/995.

BACKGROUND ART

Known processes for producing 4a-aryl-trans-decahydroisoquinolines, especially, 6-oxo compounds, include the method of Rapoport et al. (U.S. Pat. No. 4,189,583, J. Org. Chem. 42, 1485, 1977), the method of Zimmerman et al. (J. Org. Chem. 54, 1442, 1989) and the method of Judd et al. (J. Med. Chem. 35, 48, 1992).

A key step utilized in the present invention, that is, the step of introducing an aromatic ring employs the 1,4-conjugate addition reaction to an enone compound (II) using an aromatic metal compound represented by aromatic copper compounds. A process for producing 4a-aryl-6-oxodecahydroisoquinolines utilizing a reaction similar to this reaction is known (J. Org. Chem. 39, 1118, 1974., U.S. Pat. No. 4,301,290). That is, in this process, a compound of the formula (XI)

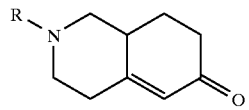

(XI)

is reacted with a aromatic copper complex to produce a 4a-aryl-6-oxodecahydroisoquinoline of the formula (XII).

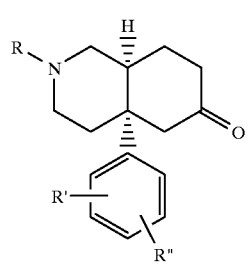

(XII)

However, the condensed ring moiety of the compound produced by this process has the cis configuration, and the trans isomers which the invention aims at producing cannot be obtained by this process.

Further, it is known that among the 4a-aryldecahydroisoquinoline compounds, the compounds having a condensed ring with cis configuration are thermodynamically stable than the compounds having a condensed ring with trans configuration.

DISCLOSURE OF THE INVENTION

An object of the present invention is to provide a process for producing 4a-aryl-trans-6-oxodecahydroisoquinoline derivatives which are useful as analgesics and/or narcotic antagonists and as materials for synthesizing immunosuppressive agents by smaller number of steps and with high yield.

The present inventors intensively studied the process for producing 4a-aryl-6-oxodecahydroisoquinoline derivatives, especially, their trans isomers. As a result, as shown in Chart 1, 1,4-conjugate addition reaction to a compound (II) derived from a compound (I) which is a starting material was attained using an aromatic metal compound, and a novel synthesis route to 4a-aryl-trans-6-oxodecahydroisoquinoline derivatives employing this reaction a key step was discovered, thereby reaching the present invention. The present invention makes it possible to synthesize 4a-aryl-trans-6-oxodecahydroisoquinolines with shorter steps than those of known process.

That is, the present invention provides a process for producing 4a-aryl-trans-6-oxodecahydroisoquinoline derivatives comprising the steps of:

reacting a compound of the formula (I)

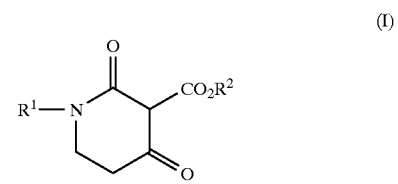

(I)

(wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl) with methylvinylketone to convert the compound of the formula (I) to a compound of the formula (II)

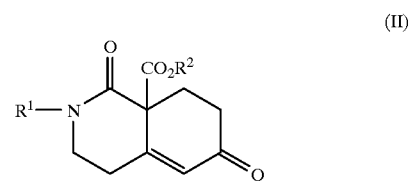

(II)

(wherein $R^1$ and $R^2$ represent the same meanings as described above);

reacting the compound of the formula (II) with an aromatic metal compound prepared from a compound of the formula (III)

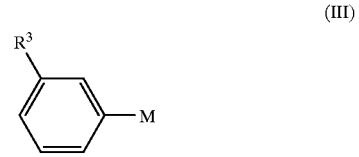

(III)

(wherein $R^3$ is hydrogen atom, $C_1$–$C_4$ alkoxy or benzyloxy group, M is lithium, magnesium chloride, magnesium bromide or magnesium iodide)

and a metal compound of which metal is selected from the metals belonging to Groups VIIB, VIII, IB, IIB and IIIA, to convert the compound (II) to a compound of the formula (IV)

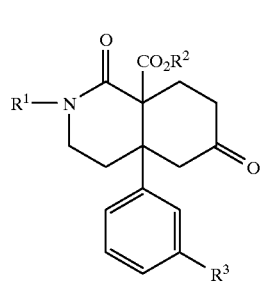

(IV)

(wherein $R^1$, $R^2$ and $R^3$ represent the same meanings as described above);

reacting the compound of the formula (IV) with an alcohol, to convert the compound of the formula (IV) to a compound of the formula (V)

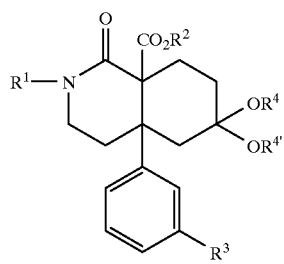

(V)

(wherein $R^1$, $R^2$ and $R^3$ represent the same meanings as described above, $R^4$ and $R^{4'}$ independently are methyl or ethyl, or R and $R^{4'}$ are bonded to form ethylene or trimethylene);

decarboxylating the compound of the formula (V), to convert the compound of the formula (V) to a compound of the formula (VI)

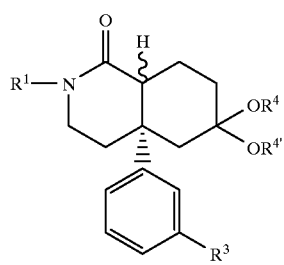

(VI)

(wherein $R^1$, $R^3$, $R^4$ and $R^{4'}$ represent the same meanings as described above);

reducing the compound of the formula (VI) to a compound of the formula (VII)

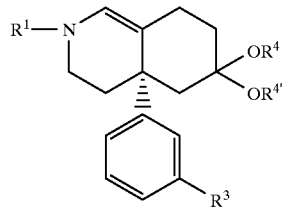

(VII)

(wherein $R^1$, $R^3$ $R^4$ and $R^{4'}$ represent the same meanings as described above);

reducing the compound of the formula (VII) to a compound of the formula (VIII)

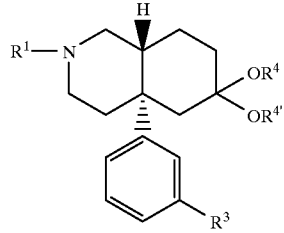

(VIII)

(wherein $R^1$, $R^3$ $R^4$ and $R^{4'}$ represent the same meanings as described above); and hydrolyzing the compound of the formula (VIII) to obtain a compound of the formula (IX)

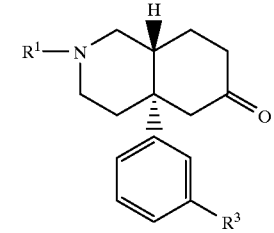

(IX)

(wherein $R^1$ and $R^3$ represent the same meanings described above).

The present invention also provides a process for producing 4a-aryl-trans-6-oxodecahydroisoquinoline derivatives comprising the steps of cleaving the phenol ether bond of the compound (VIII) obtained in the above-described process, in which $R^3$ is $C_1$–$C_4$ alkoxy or benzyloxy group, to convert the compound of the formula (VIII) to a compound of the formula (X)

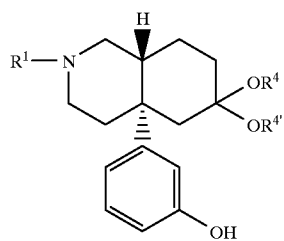

(wherein $R^1$, $R^4$ and $R^{4'}$ represent the same meanings described above); and hydrolyzing the compound of the formula (X) to obtain the compound of the formula (IX)

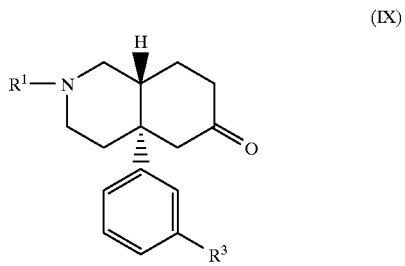

(wherein $R^1$ represents the same meaning as described above, and $R^3$ is hydroxyl group).

By the present invention, 4a-aryl-trans-6-oxodecahydroisoquinoline derivatives which are useful as analgesics and as materials for synthesizinc immunosuppressive agents and the like may be produced with short steps in high yield.

BEST MODE FOR CARRYING OUT THE INVENTION

Preferred examples of $R^1$ in the formula (I) include methyl, ethyl, (n-, iso-)propyl, (n-, iso-, sec-, tert-)butyl, n-pentyl, n-hexyl, allyl, benzyl, phenethyl, cyclopropylmethyl, cyclobutylmethyl, cyclopentylmethyl and cyclohexylmethyl groups. Among these, benzyl and cyclopropylmethyl groups are especially preferred.

Examples of $R^2$ include methyl, ethyl, n-propyl, n-butyl and benzyl groups. Among these, ethyl group is especially preferred.

Examples of $R^3$ include hydrogen atom, methoxy, ethoxy, (n-, iso-)propoxy, (n-, iso-, sec-, tert-)butoxy and benzyloxy groups. Among these, hydrogen atom and methoxy group are especially preferred. Examples of $R^4$, $R^{4'}$ in the formula (IV) include independently methyl and ethyl, and that $R^4$ and $R^{4'}$ are bonded to ethylene or trimethylene. Among these, ethylene formation are especially preferred.

The 4a-aryldecahydroisoquinoline derivatives obtained by the present invention are numbered in general as shown in the formula below, and their basic skeleton is 1,2,3,4,4a,5,6,7,8,8a-decahydroisoquinoline.

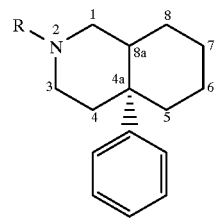

Although each of the structural formulae in the is present invention shows only one of the optical isomers, the formulae include d-enantiomers, l-enantiomers and dl-compounds, and the "RS" which indicates the absolute configuration is omitted in the above-mentioned nomenclature.

The process for producing 2-alkyl-4a-aryl-trans-6-oxodecahydroisoquinoline derivatives utilizing the present invention is carried out by the steps concretely shown in Chart 1.

Chart 1

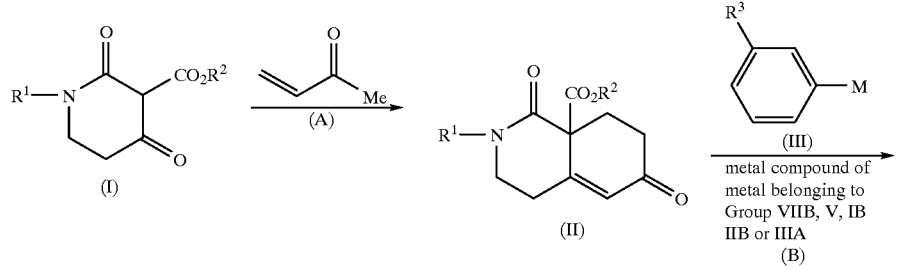

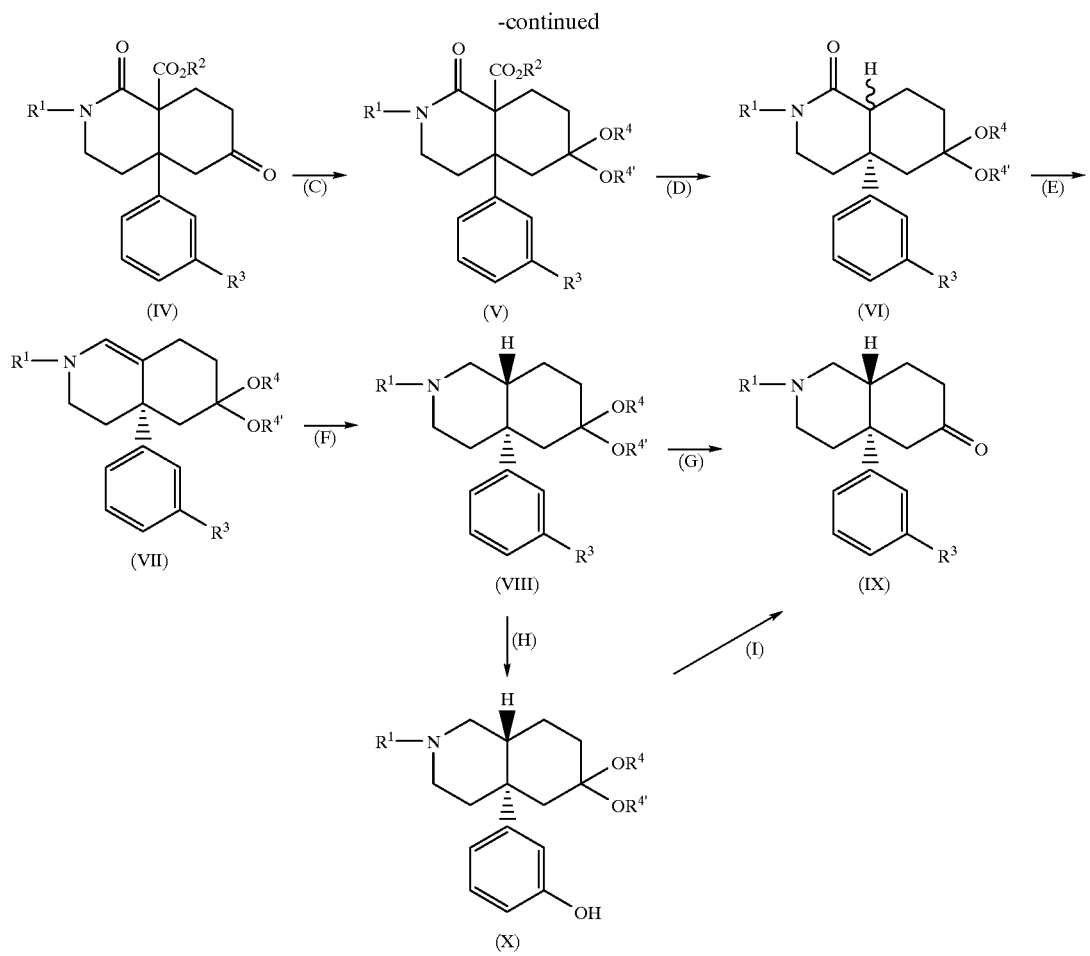

The first step (A) is the step in which the material (I) obtained by the method of Schultz et al. (J. Org. Chem., 50, 217, 1985) is reacted with methylvinylketone to convert the compound (I) to 2-alkyl-8a-carboalkoxy-1,6-dioxo-1,2,3,4, 6,7,8,8a-octahydroisoquinoline derivative (II). This step is divided into a conjugate addition reaction between the material (I) and methylvinylketone, intramolecular cyclization reaction and dehydration reaction. Although each of these steps is described in the above-mentioned report (J. Org. Chem., 50, 217, 1985), the yield is low.

The present inventors thought that the cause of the low yield in the step (A) carried out by Schultz et al. resides in the conjugate addition reaction step and studied the reaction conditions in this step. As a result, reaction conditions by which the isolation yield of the compound (II) is largely increased were successfully discovered. The reaction conditions include a method in which the compound of the formula (I) is reacted with methylvinylketone in the presence of an inorganic base or a metal alkoxide, and in the presence of a crown ether (Method 1); a method in which the compound of the formula (I) is reacted with methylvinylketone in the presence of a corresponding metal alkoxide in alcohol (Method 2); and a method in which the compound of the formula (I) is reacted with methylvinylketone in the presence of an alkaline metal fluoride (Method 3). The Methods 1 and 3 are preferred.

Preferred examples of the inorganic base which may be employed in the Method 1 include potassium hydroxide, sodium hydroxide, lithium hydroxide, calcium hydroxide, barium hydroxide, potassium carbonate, sodium carbonate and lithium carbonate. Among these, potassium hydroxide is especially preferred. In cases where a metal alkoxide is used as the base, potassium (n-, tert-)butoxide, potassium methoxide, potassium ethoxide, potassium n-propoxide, potassium benzyl alkoxide, sodium (n-, tert-)butoxide, sodium methoxide, sodium ethoxide, sodium n-propoxide, sodium benzyl alkoxide, lithium (n-, tert-)butoxide, lithium methoxide, lithium ethoxide, lithium n-propoxide and lithium benzyl alkoxide may be employed. Although an alkoxide corresponding to the ester moiety ($CO_2R^2$) of the substrate (I) or tert-butoxide is preferred, the metal alkoxide is not restricted thereto. As the crown ether, any known crown ethers such as 18-crown-6, 12-crown-4, 15-crown-5, benzo-12-crown-4, benzo-15-crown-5, benzo-18-crown-6, 4'-bromobenzo-18-crown-6, dibenzo-18-crown-6, dibenzo-24-crown-8, dibenzo-30-crown-10, dicyclohexano-18-crown-6 and dicyclohexano-24-crown-8 may be employed. The crown ether may be appropriately selected depending on the metal ion species of the base employed. As for the combination of the base and the crown ether, potassium hydroxide/18-crown-6 is especially preferred, although the combination is not restricted thereto. The molar ratio of substrate (I)/base/crown ether may preferably be 1 mol/0.01–1 mol/0.01–1 mol equivalent, and 1 mol/0.1 mol/0.1 mol equivalent is especially preferred. The amount of methylvinylketone is at least one equivalent, preferably 2 to 3 equivalents. Preferred solvents are polar solvents such as alcohols, dimethylformamide and dimethylsulfoxide, and ether solvents such as diethyl ether, tetrahydrofuran and 1,4-dioxane. Alcohols corresponding to the ester moiety ($CO_2R^2$) of the substrate (I) are especially preferred. However, when tert-butoxide is used as the base, tert-butanol is preferred. The reaction temperature is preferably 0–80° C. and the reaction is usually carried out at room temperature. The reaction time may be 5–72 hours, usually 10–24 hours.

The alcohols which may be used in Method 2 are the alcohols ($R^2OH$) corresponding to the ester moiety of the substrate (I), such as methanol, ethanol, n-propanol, n-butanol, benzyl alcohol and the like. Examples of the alkoxide include sodium methoxide, sodium ethoxide, sodium n-propoxide, sodium n-butoxide, sodium benzyl alkoxide, potassium methoxide, potassium ethoxide, potassium n-propoxide, potassium n-butoxide, potassium benzyl alkoxide, lithium methoxide, lithium ethoxide, lithium n-propoxide, lithium n-butoxide, lithium benzyl alkoxide and the like. The molar ratio of substrate (I)/alkoxide is preferably 1 mol/0.01–1 mol equivalent, and 1 mol/0.1 mol equivalent is especially preferred. The amount of methylvinylketone is at least one equivalent, preferably 2 to 3 equivalents. The reaction temperature is preferably 0–50° C. and the reaction is usually carried out at room temperature. The reaction time may be 5–72 hours, usually 5–24 hours.

Preferred examples of the alkaline metal fluoride which may be employed in Method 3 include lithium fluoride, sodium fluoride and potassium fluoride. Among these, potassium fluoride is especially preferred. An crown ether may be added to the reaction system. In this case, any of the known crown ethers may be added and the crown ether may appropriately be selected depending on the metal ion species of the fluoride. Especially, potassium fluoride/18-crown-6 is preferred. The molar ratio of substrate (I)/alkaline metal fluoride/18-crown-6 is preferably 1 mol/0.01–1 mol/0.01–1 mol equivalent, and 1 mol/0.2 mol/0.2 mol equivalent is especially preferred. The amount of methylvinylketone is at least one equivalent, preferably 1.5 to 3 equivalents, especially 2 equivalents. As the solvent, polar solvents such as alcohols, dimethylformamide and dimethyl sulfoxide; ether solvents such as diethyl ether, tetrahydrofuran and 1,4-dioxane; and non-polar solvents such as benzene, toluene, xylene, dichloromethane and chloroform are preferred. Among these, toluene is especially preferred. The reaction temperature is preferably 0–80° C. and the reaction is usually carried out at room temperature. The reaction time may be 5–120 hours, usually 10–36 hours.

The above-described three methods are improved methods in the step of the conjugate addition reaction between the substrate (I) and methylvinylketone, and the subsequent steps for completing the step (A) are carried out according to the method by Schultz et al. (J. Org. Chem., 50, 217, 1985). That is, the intermediate of the step (A) obtained by the conjugate addition reaction step is treated with pyrrolidine under reflux in benzene without being purified, and acetic acid/water/sodium acetate mixture is added thereto, followed by heating the resulting mixture. The purification of the compound (II) obtained by this operation may be carried out by silica gel chromatography or by recrystallization method, although the purification method is not restricted thereto.

The next step (B) is the synthesis step for obtaining 2-alkyl-4a-aryl-8a-carboalkoxy-1,6-dioxo-1,2,3,4,4a,5,6,7,8,8a-decahydroisoquinoline derivative (IV) by the 1,4-conjugate addition reaction to the 2-alkyl-8a-carboalkoxy-1,6-dioxo-1,2,3,4,6,7,8,8a-octahydroisoquinoline derivative (II) using an aromatic metal compound prepared from the compound of the formula (III) and a metal compound of which metal is selected from the metals belonging to the Groups VIIB, VIII, IB, IIB and IIIA.

As the metal M represented by the formula (III), lithium (Li), magnesium chloride (MgCl), magnesium bromide (MgBr) and magnesium iodide (MgI) are preferred. In cases where a metal compound of which metal is belonging to Group VIIB is used as the metal compound necessary for the 1,4-conjugate addition of the compound (III) to the compound (II), although the metal compound is not restricted as long as the metal is divalent, the metal compound is preferably a divalent manganese compound, and may be an ate complex. In cases where a metal compound of which metal belongs to Group IB is used, although the metal is not restricted as long as it is monovalent, the metal compound is preferably a monovalent copper compound, and the metal compound may be an ate complex. The monovalent copper compound may be added as a catalyst to the compound of the formula (III) or may be added as a catalyst to the aromatic metal compound prepared from the compound of the formula (III) and the metal compound of which metal belongs to Group VIIB or IIB. In cases where a metal compound of which metal belongs to Group IIB is used, although the metal compound is not restricted as long as it is divalent, a divalent zinc compound is preferred, and the metal compound may be an ate complex. In cases where a metal compound of which metal belongs to Group IIIA is used, although the metal compound is not restricted as long as it is trivalent, trivalent aluminum compounds are preferred, and the metal compound may be an ate complex. In cases where a metal compound of which metal belongs to Group VIII is used, although the metal compound is not restricted as long as it is divalent, divalent iron compounds, cobalt compounds, nickel compounds and paradium compounds are preferred. The divalent cobalt compounds, nickel compounds and paradium compounds may be added as catalysts to the aromatic metal compound prepared from the compound of the formula (III) and the metal compound of which metal belongs to Group IIB or IIIA. Among the monovalent copper compounds, divalent manganese compounds, divalent zinc compounds and trivalent aluminum compounds which are necessary for proceeding the 1,4-conjugate addition, monovalent copper compounds and divalent manganese compounds are especially preferred. The above-mentioned metal compounds may preferably be in the form of metal halogenide, metal carboxylate, metal alkoxide, metal mercaptide, metal acetylide or metal cyanide, although the forms of the metal compound are not restricted thereto.

In the step (B), in cases where $R^3$ of the compound (III) is hydrogen atom, the aromatic copper compound may be prepared by adding phenyl lithium (1.0 M solution in cyclohexane/ether) to a suspension of the copper compound in an ether solvent. Further, by adding a solution of the compound (II) in an ether solvent to the thus prepared mixture of the aromatic copper compound, the 1,4-conjugate addition reaction proceeds and the compound (IV) ($R^3$=H) is generated. The molar ratio of substrate (II)/phenyl lithium/copper compound is 1 mol/2–6 mol/1–3 mol equivalent, preferably 1 mol/4 mol/2 mol equivalent. Examples of the copper compound which may be employed include cuprous iodide, cuprous bromide-dimethylsulfide complex, cuprous chloride, cuprous cyanide, 2-thienyl(cyano)cuprous lithium, copper(I) acetylides, alkynyl(cyano)cuprous lithiums and the like. Among these, cuprous iodide is preferred. Preferred examples of the reaction solvent include ether solvents such as diethyl ether, tetrahydrofuran, dimethoxyethane, 1,4- dioxane and the like. Among these, diethyl ether is preferred. However, depending on the solubility of the substrate, diethyl ether/tetrahydrofuran mixed solvent may be used. The reaction temperature is preferably −50° C. to 0° C., more preferably −20° C. to 0° C. during preparation of the aromatic copper compound. During the 1,4-conjugate addition reaction, the reaction temperature is preferably −10° C. to 30° C., and satisfactory results may usually be obtained at room temperature. As a reaction accelerator, chlorotrimethylsilane, boron trifluoride ether complex, hexamethylphosphortriamide, triphenylphosphine, tributylphosphine or the like may be used individually or in combination. Among these, chlorotrimethylsilane is especially preferred. In this case, the reaction temperature during the 1,4-conjugate addition reaction may preferably be gradually raised within the range between −78° C. and room temperature. The reaction accelerator may preferably be used in an amount of 2 mol to 5 mol equivalents, more preferably 3 mol to 4 mol equivalent. The reaction time may be 1–72 hours, usually 2–24 hours. The method of purifying the compound (IV) ($R^3$=H) is not restricted and this compound may be isolated by recrystallization method or silica gel column chromatography, preferably by recrystallization method.

In cases where $R^3$ of the compound (III) is $C_1$–$C_4$ alkoxy or benzyloxy group, the aromatic copper compound may be prepared by, for example, reacting m-alkoxybromobenzene with an alkyl lithium in an ether solvent at −78° C. to 0° C., preferably −78° C. to −50° C. so as to carry out metal-halogen exchange reaction to obtain the compound (III) ($R^3$: $C_1$–$C_4$ alkoxy group or benzyloxy group, M: lithium) and by adding this compound to a suspension of the copper compound in an ether solvent. By adding a solution of the compound (II) in an ether solvent to the thus obtained mixture of the aromatic copper compound, the 1,4-conjugate addition reaction proceeds so that the compound (IV) ($R^3$: $C_1$–$C_4$ alkoxy or benzyloxy group) is generated. In this case, a reaction accelerator may be added. The molar ratio of substrate (I)/m-alkoxybromobenzene/alkyl lithium/copper compound/reaction accelerator may be 1 mol/2–6 mol/2–6 mol/1–3 mol/3–5 mol equivalent, preferably 1 mol/4 mol/4 mol/2 mol/4 mol equivalent. As the alkyl lithium, (n-, sec, tert-)butyllithiums may preferably be employed, and tert-butyllithium is especially preferred. In this case, it is preferred to use tert-butyllithium in an amount of twice by mole of m-alkoxybromobenzene. Examples of the copper compound which may be employed include cuprous iodide, cuprous bromide-dimethylsulfide complex, cuprous chloride, cuprous cyanide, 2-thienyl(cyano)cuprous lithium, copper(I) acetylides, alkynyl(cyano)cuprous lithiums and the like. Among these, cuprous iodide is preferred. Preferred examples of the reaction accelerator for the 1,4-conjugate addition reaction include boron trifluoride ether complex, chlorotrimethylsilane, hexamethylphosphortriamide, triphenylphosphine and tributylphosphine, and these may be used individually or in combination. Among these, chlorotrimethylsilane is especially preferred. Preferred examples of the reaction solvent include ether solvents such as diethyl ether, tetrahydrofuran, dimethoxyethane, 1,4-dioxane and the like. Among these, diethyl ether is preferred for the conjugate addition reaction. However, depending on the solubility of the substrate, diethyl ether/tetrahydrofuran mixed solvent may be used. The reaction temperature is preferably gradually raised in the range between −78° C. and room temperature during the metal halogen exchange reaction. During the preparation of the complex, the reaction temperature is preferably −50° C. to 0° C., more preferably −20° C. to 0° C. During the 1,4-conjugate addition reaction, the reaction temperature is preferably −10° C. to 30° C., and satisfactory results are usually obtained at room temperature. The reaction time may be 30 minutes to 72 hours, usually 2–24 hours. The method of purifying the compound (IV) ($R^3$: $C_1$–$C_4$ alkoxy or benzyloxy group) is not restricted and this compound may be isolated by recrystallization method or silica gel column chromatography.

The aromatic manganese complex compounds may be prepared, for example, as follows: First, chlorobenzene, bromobenzene, iodobenzene, m-alkoxychlorobenz(ene, m-alkoxybromobenzene or m-alkoxyiodobenzene is reacted with magnesium in an ether solvent at a temperature between room temperature and refluxing condition to obtain the compound (III) ($R^3$: hydrogen, $C_1$–$C_4$ alkoxy or benzyloxy group, M: magnesium chloride, magnesium bromide or magnesium iodide). By adding the obtained compound to a solution of the compound (II), a divalent manganese compound, lithium chloride and cuprous chloride in ether, 1,4-conjugate addition reaction proceeds and the compound (IV) ($R^3$: hydrogen, $C_1$–$C_4$ alkoxy or benzyloxy group) is generated. In this case, the reaction accelerator mentioned above may be added. The molar ratio of substrate (II)/aromatic bromide/magnesium/diveLlent manganese compound/lithium chloride/cuprous chloride may be 1 mol/1–5 mol/1–5 mol/0.5–1.5 mol/3–9 mol/0.1–1.5 mol equivalent, preferably 1 mol/2.4 mol/2.9 mol/1.1 mol/6 mol/1.1 mol equivalent. Examples of the divalent manganese compound include manganese chloride, manganese bromide and manganese iodide, and manganese chloride is preferred. As a preferred reaction accelerator for the 1,4-conjugate addition reaction, chlorotrimethylsilane may be used in an amount of 1–5 equivalents, more preferably 3 equivalents. As the reaction solvent, ether solvents such as diethyl ether, tetrahydrofuran, dimethoxyethane and 1,4-dioxane may be employed individually or in combination. Among these, tetrahydrofuran and dimethoxyethane are especially preferred. The reaction temperature is preferably −30° C. to 30° C., and satisfactory results are usually obtained at 0° C. to room temperature. The reaction time may be 30 minutes to 72 hours, usually 1–24 hours. The method of purifying the compound (IV) ($R^3$: hydrogen, $C_1$–$C_4$ alkoxy or benzyloxy group) is not restricted and this compound may be isolated by recrystallization method or silica gel column chromatography.

The next step (C) is the step of protecting the carbonyl group at the 6-position of the compound (IV) by ketal-forming reaction so as to convert it to the compound (V). Here, $R^4$ and $R^{4'}$ individually represent linear alkyl group such as methyl or ethyl, or $R^4$ and $R^{4'}$ are bonded together to form ethylene or trimethylene. As the ketal-protecting group, an acyclic ketal such as dimethylacetal or diethylacetal, or a cyclic ketal such as ethylene ketal or trimethylene ketal may be employed. Among these, cyclic ketals such as ethylene ketal and trimethylene ketal are preferred, and ethylene ketal is especially preferred. More particularly, the compound (IV) is dissolved in an aromatic hydrocarbon solvent such as benzene, toluene or xylene together with an alcohol such as methanol, ethanol, ethylene glycol, trimethylene glycol or the like, and an acid catalyst is added. By heating the resulting mixture under stirring while evaporating off the generated water by azeotropic distillation, the compound (V) is obtained. In cases where an acyclic ketal is employed, the compound (V) may also be obtained by heating a mixture of the compound (IV) and an orthoester such as methyl orthoformate, ethyl orthoformate, methyl orthoacetate or ethyl orthoacetate in an alcohol solvent such as methanol or ethanol in the presence of an acid catalyst. As an acid catalyst used in these cases, inorganic acids such as hydrochloric acid, sulfuric acid and phosphoric acid, and organic acids such as methanesulfonic acid, benzenesulfonic acid, p-toluenesulfonic acid and camphorsulfonic acid may usually be used. Among these, hydrochloric acid, methanesulfonic acid, camphorsulfonic acid and p-toluenesulfonic acid are preferred, and p-toluenesulfonic acid is especially preferred. The reaction temperature may be 20° C. to 150° C., and especially, satisfactory results are obtained at 60° C. to 130° C. The reaction time may be 2–72 hours, usually 2–5 hours. The compound (V) obtained by the above-described reaction may be used in the next step without being purified. However, in cases where the compound (V) is purified, the purification may be carried out by applying the compound to a short column employing silica gel.

The next step (D) is the step of removing the carboalkoxy group at 8a-position to convert the compound (V) to the compound (VI). This conversion may be carried out by the method described in a reference (P. A. Bartlett, W. J. Johnson, Tetrahedoron Lett., 4459, 1970). That is, the compound (V) is reacted with a metal alkyl mercaptide. Examples of the alkyl mercaptan which may be employed include ethyl mercaptan, n-propyl mercaptan, isopropyl mercaptan, n-butyl mercaptan, isobutyl mercaptan, tert-butyl mercaptan and the like. Among these, ethyl mercaptan is preferred, although the alkyl mercaptan is not restricted thereto. Preferred examples of the base include sodium hydride, sodium hexamethyldisilamide, potassium hydride, potassium hexamethyldisilamide, potassium tert-butoxide and the like. Among these, sodium hydride is especially preferred, although the base is not restricted thereto. The equivalent of the metal alkyl mercaptide used may be at least equimolar to excess with respect to the substrate, and to use 6 molar equivalents is preferred. As the reaction solvent, aprotic polar solvents such as dimethylformamide, N-methyl- 2-pyrrolidone are preferred, and dimetliylformamide is especially preferred. The reaction temperature may be 60° C. to 120° C., usually 80° C. The reaction time may be 1–72 hours, usually 4–10 hours.

The next step (E) is the step of reducing the carbonyl group at the 1-position of the compouand (VI) so as to convert the compound (VI) to the enamine compound (VII). This step may be carried out according to the method of Rapoport et al. (U.S. Pat. No. 4,189,583, J. Org. Chem. 42, 1485, 1977). That is, diisobutylalijminum hydride is used as a reducing agent in amount not less than equimolar, preferably 5 molar equivalents with respect to the substrate (VI). As the solvent, ether solvents such as diethyl ether, tetrahydrofuran, dimethoxy ethane and the like may be employed. Among these, tetrahydrofuran is preferred. The reaction temperature may be 0° C. to room temperature. The obtained compound (VII) may be subjected to the next step (F) without being purified.

The step (F) is the step of reducing the enamine compound (VII) so as to convert it to trans-4a-aryldecahydroisoquinoline compound (VIII). A, known method for carrying out this conversion is the catalytic hydrogenation method by Rapoport et al. (U.S. Pat. No. 4,189,583, J. Org. Chem. 42, 1485, 1977) which uses 5% rhodium/alumina catalyst, and similar known methods include the catalytic hydrogenation method by Zimmerman et al. (J. Org. Chem., 54, 1442, 1989) which uses platinum oxide catalyst, and the hydride reduction method by Evans, Zimmerman et al. (J. Am. Chem. Soc., 102, 5955, 1980) which uses sodium borohydride in the presence of perchloric acid. The present inventors studied the methods carrying out this conversion to discover a novel method for reduction which has a good reproducibility. That is, the enamine compound (VII) is reduced with sodium cyanoborohydride. Sodium cyanoborohydride may be used in an amount of 0.5 to 5 molar equivalents, preferably 1 to 3 molar equivalents per one mole of the substrate (VII). As the reaction solvent, polar solvents such as methanol, ethanol and dimethylformamide are preferred. Among these, methanol is especially preferred. For proceeding the reaction, it is preferred to keep the mixture in acidic condition. More particularly, it is preferred to keep the pH of the reaction solution to 2–5, especially about 4 by adding methanol saturated with hydrochloric acid. Needless to say, the acid which may be employed is not restricted to hydrochloric acid. The reaction temperature may be −20° C. to room temperature, usually −10° C. to 0° C.

The step (G) is the step of removing the acetal-protecting group after dissolving the compound (VIII) in a solvent in the presence of an acid catalyst so as to convert the compound (VIII) to the 4a-aryldecahydroisoquinoline derivative (IX). Examples of the acid catalyst include inorganic acids such as sulfuric acid, hydrochloric acid and phosphoric acid; organic sulfonic acids such as methanesulfonic acid, benzenesulfonic acid, p-toluenesulfonic acid and camphorsulfonic acid; and organic carboxylic acids such as acetic acid and propionic acid. Sufficiently satisfactory results may usually be obtained by using sulfuric acid or hydrochloric acid. As the solvent, mixed solvents of water and an ether solvent such as diethyl ether, tetrahydrofuran, dimethoxyethane and 1,4-dioxane; and mixed solvents of water and a halogen-containing solvent such as dichloromethane, chloroform, carbon tetrachloride and 1,2-dichloroethane, or acidic aqueous solution containing the above-described acid catalyst may be employed. Usually, sufficiently satisfactory results may be obtained by using dilute aqueous sulfuric acid or dilute hydrochloric acid. The reaction may be carried out at a temperature between −50° C. and 100° C., and satisfactory results may usually be obtained at 0° C. to 50° C.

The step (H) is to cleave the phenol ether bond of the compound (VIII) in which $R^3$ is $C_1$–$C_4$ alkoxy or benzyloxy group so as to convert the compound (VIII) to the compound (X). That is, this step may be carried out by dissolving the compound (VIII) in a solvent and reacting with a base in the presence of a mercaptan or a trivalent boron compound. If a trivalent boron compound is used, the subsequent step (I) can be omitted. As the solvent, in cases where mercaptan and a base are used, aprotic polar solvents such as dimetylformamide, dimethylsulfoxide and hexamethylphosphortriamide are preferred, and dimethylformamide is especially preferred. In cases where a trivalent boron compound is used, halogen-containing solvents such as dichloromethane, chloroform and carbon tetrachloride are preferred, and dichloromethane is especially preferred. As the mercaptan, those having linear $C_1$–$C_{10}$ side chains are preferred, and usually, propyl mercaptan is preferably employed. Examples of the base include alkaline metal salts of alcohols such as potassium tert-butoxide, potassium ethoxide, sodium tert-butoxide, sodium ethoxide and sodium methoxide; hydrides such as sodium hydride and potassium hydride; and metal salts of ammonia such as sodium amide. Usually, sufficiently satisfactory results may be obtained by using tert-butoxide. Examples of the trivalent boron compound include boron tribromide and boron trichloride, and boron tribromide is especially preferred. In cases where mercaptan is used, the reaction temperature may be 0° C. to 300° C., preferably 50° C. to 200° C., more preferably 80° C. to 120° C. In cases where a trivalent boron compound is used, the reaction temperature may preferably be −80° C. to 50° C., especially 0° C. to 30° C.

The next step (I) is to remove the acetal-protecting group at the 6-position by dissolving the compound (X) in a solvent together with an acid catalyst so as to convert the compound (X) to the compound of the formula (IX) in which $R^3$ is hydroxyl group. This step may be carried out in the same manner as in the step (G) shown in Chart 1. Purification of the compound (IX) may easily be carried out by silica gel column chromatography or recrystallization, or by first converting the compound to a pharmaceutically acceptable salt and then subjecting the resultant to recrystallization.

The 4a-aryl-trans-6-oxodecahydroisoquinoline derivatives obtained by the present invention are useful as analgesics and/or narcotic antagonists as disclosed in Japanese Laid-open Patent Application (Kokai) No. 5-155857, and as materials for synthesizing immunosuppressive agents disclosed in WO 89/995.

EXAMPLES

The present invention will be described more concretely by way of reference examples and examples. It should be noted that these examples are presented for the illustration purpose only and should not be interpreted in any restrictive way.

Reference Example 1
Ethyl 3-(benzylamino) Propionate 1

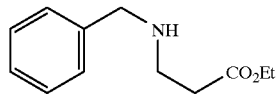

1

To a solution containing 13.9 g (129.84 mmol) of benzylamine in 30 ml of ethanol, 10 g (99.88 mmol) of ethyl acrylate was slowly dropped at 50° C. for 1 hour under stirring. After the dropping, the mixture was heated at 80° C. for 1 hour. After the reaction, the reaction solution was cooled to room temperature and the solvent was evaporated under reduced pressure to obtain a residue in the form of oil. By distilling the residue under reduced pressure, excess benzylamine was recovered as the initial fraction (50–60° C., 0.75 mmHg) and then the captioned compound was obtained as a colorless oil at 129–133° C. (0.75 mmHg).

Yield: 17.4 g Yield: 84.2%; bp. 129–133 ° C. (0.75 mmHg); IR (liquid film method); ν max cm$^{-1}$:1734. NMR (90 MHz, CDCl3); δ:1.26(3H, t, J=7.0 Hz), 1.70(1H, br s), 2.53(2H, t, J=5.8 Hz), 2.91(2H, t, J=5.8 Hz), 3.82(2H, s), 4.16(2H, q, J=7.0 Hz), 7.31 (5H, s). Mass(EI); m/z: 207(M$^+$)

Reference Example 2
Ethyl 3-{(N-cyclopropylmethyl)amino} Propionate 2

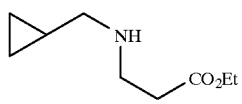

2

By the operation similar to Reference Example 1, the captioned compound was obtained as a colorless oil from 5 g (70.3 mmol) of cyclopropylmethylamine, 6.12 g (61.13 mmol) ethyl acrylate and 25 ml of ethanol.

Yield: 9.39 g Yield: 90%; bp. 68.5–70° C. (0.75 mmHg); IR (liquid film method); ν max cm$^{-1}$:3500, 1736. NMR(90 MHz, CDCl3); δ:0.08–0.20(2H, m), 0.40–0.60(2H, m), 0.96 (1H, m), 1.27(3H, t, J=7.0 Hz), 2.46(2H, t, J=5.0 Hz), 2.53(2H, t, J=5.0 Hz), 2.92(2H, t, J=6.3 Hz), 3.61(1H, s), 4.17(2H, q, J=7.0 Hz). Mass(EI); m/z:171(M$^+$)

Reference Example 3
Ethyl 3-(N-benzyl-N-carboethoxyacetamide) Propionate 3

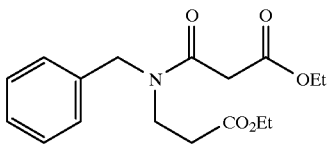

3

To a solution containing 2.07 g (10 mmol) of ethyl 3-(benzylamino) propionate 1 and 1.39 g (10.5 mmol) of monoethyl malonate in 40 ml of ethyl acetate, a solution containing 2.17 g (10.5 mmol) of dicyclohexylcarbodiimide in 10 ml of ethyl acetate was dropped under stirring while cooling the mixture in ice. The reaction mixture was then stirred at room temperature for 12 hours. The precipitates of an urea derivative resulting from the reaction was filtered with suction through a 3G4 glass filter, and the mother liquor was concentrated under reduced pressure to obtain a residue. The obtained residue was mixed with ethyl acetate/hexane= 1:2, and the generated precipitates were treated as described above to obtain the captioned compound as a colorless oil.

Yield: 3.26 g Yield 100%; IR (liquid film method); ν max cm$^{-1}$:1738,1653. NMR(90 MHz, CDCl3); δ:1.17–1.39(6H, m), 2.46–2.73(2H, m), 3.37–3.74(2H, m), 3.44 an d 3.65 (2H, each s), 4.00–4.30(4H, m), 4.61 and 4.65(2H, each s), 7.20–7.40(5H, m). Mass (EI); m/z:321(M$^+$)

Reference Example 4
Ethyl 3-(N-cyclopropylmethyl-N-carbomethoxyacetamide) Propionate 4

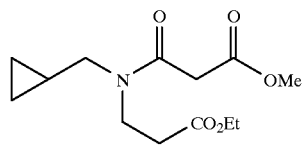

4

To a solution containing 5 g (29 mmol) of ethyl 3-{ (cyclopropylmethyl)amino} propionate and 10 ml (71.9 mmol) of triethylamine in 100 ml of dichloromethane, 5.95 g (43.6 mmol) of methylmalonyl chloride was dropped at 0° C., and the obtained mixture was stirred at room temperature for 6 hours. After the reaction, the reaction solution was washed with 1N hydrochloric acid, 1N sodium hydroxide and with saturated saline, and the resultant was dried over sodium hydrogen sulfate. After filtration, the solvent was evaporated under reduced pressure to obtain 9.96 g of oil and the obtained oil was subjected chromatography (cyclohexane/ethyl acetate=3:1–2:1 v/v) using 200 g of silica gel, to obtain the captioned compound as a colorless oil.

Yield: 6.58 g Yield: 84%; IR (liquid film method); ν max cm$^{-1}$:1734,1653. NMR(90 MHz, CDCl3); δ:0.141–0.35 (2H, m), 0.42–0.67(2H, m), 0.94(1H, m), 1.25(3H, t, J=6.3 Hz), 2.63(0.7H, t, J=6.3 Hz), 2.66(1.3H, t, J=6.3 Hz), 3.24(2H, t, J=6.3 Hz), 3.47(1.3H, s), 3.57(0.7H, s), 3.69

(1.3H, d, J=7.3 Hz), 4.12(1.3H, q, J=6.3 Hz), 4.16(0.7H, q, J=6.3 Hz), 6.74(0.7H, d, J=5.5 Hz), 6.75(3H, s). Mass (EI); m/z:271(M⁺)

Reference Example 5
Ethyl 3-(N-cyclopropylmethyl-N-carboethoxyacetamide) Propionate 5

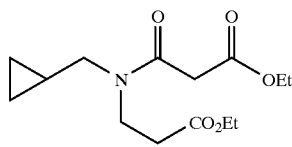

Operation 1
By the operation similar to Reference Example 3, the captioned compound was obtained as a colorless oil from 2.71 g (15.85 mmol) of ethyl 3-{(cyclopropylmethyl) amino} propionate 2, 2.09 g (15.81 mmol) of monoethyl malonate and 3.27 g (15.85 mmol) of dicyclohexylcarbodiimide.

Operation 2
In 35 ml of dichloromethane, 4.5 g (26.:31 mmol) of ethyl 3-{(cyclopropylmethyl)amino}propionate 2 and 3.66 g (27.7 mmol) of monoethyl malonate were dissolved and a solution containing 5.04 g (26.31 mmol) of 1-(3-dimethylaminopropyl)-3-ethylcarbodiimide hydrochloric acid salt in 35 ml of dichloromethane was dropped at room temperature. Three hours later, the reaction mixture was poured to ethyl acetate and the resulting mixture was washed with 1N hydrochloric acid, saturated aqueous sodium hydrogen carbonate solution and with saturated saline, followed by drying over magnesium sulfate. After filtration, the mixture was distilled under reduced pressure to evaporate the solvent to obtain the captioned compound as a colorless oil.

Yield: Operation 1 4.29 g (95%) Operation 2 7.48 g (99.8%) IR (liquid film method); ν max cm⁻¹:1738,1649. NMR(90 MHz, CDCl3); δ:0.20–0.37(2H, m), 0.42–0.67 (2H, m), 1.02(1H, m) 1.29(6H, t, J=6.0 Hz), 2.48–2.75(2H, m), 3.18–3.35(2H, m), 3.47(1.2H, s), 3.54(0.8H, s), 3.60–3.78(2H, m), 4.16(1.6H, q, J=6.0 Hz), 4.21(2.4H, q, J=6.0 Hz). Mass(EI); m/z:285(M⁺)

Reference Example 6
1-benzyl-3-carboethoxy-2,4-piperidinedione 6

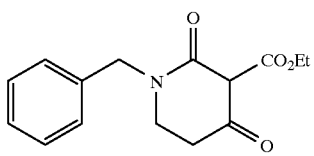

In 10 ml of anhydrous ethanol, 280 mg (12.15 mmol) of sodium metal was dissolved and a solution containing 3.25 g (10.13 mmol) of ethyl 3-(N-benzyl-N-carboethoxyacetamide) propionate 3 in anhydrous benzene was added dropwise to the mixture under argon stream under stirring while cooling the mixture in ice. After the dropping, the mixture was stirred at room temperature for 1.5 hours, to precipitate sodium salt of cyclized product. After concentrating the mixture under reduced pressure, the obtained residue was dissolved in water and washed with ether. The aqueous layer was acidified with concentrated hydrochloric acid and extracted with ethyl acetate. The organic layer was washed three times or more with saturated saline and dried over magnesium sulfate, followed by evaporating the organic solvent under reduced pressure to obtain sufficiently pure captioned compound as a colorless oil.

Yield 2.73 g Yield 99.3%; IR (liquid film method); ν max cm⁻¹:1729, 1657, 1599. NMR(90 MHz, CDCl3); δ:1.42(3H, t, J=7.2 Hz), 2.57(2H, t, J=6.7 Hz), 3.33(2H, t, J=6.7 Hz), 4.41(2H, t, J=7.2 Hz), 4.64(2H, s), 7.29(5H, s), 14.05(1H, s). Mass(EI); m/z:275(M⁺)

Reference Example 7
3-carbomethoxy-1-cyclopropylmethyl-2,4-piperidinedione 7

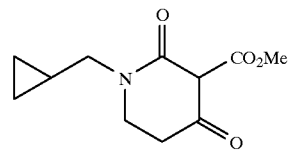

In anhydrous methanol, 298 mg (12.96 mmol) of sodium metal was dissolved and 50 ml of a solution containing 2.93 g (10.81 mmol) of ethyl 3-(N-cyclopropylmethyl-N-carbomethoxyacetamide) propionate 4 in anhydrous benzene was added thereto dropwise at 0° C., followed by stirring the obtained mixture for 2 hours. The reaction mixture was distilled under reduced pressure to obtain 2.89 g of sodium salt of cyclized product. The obtained crude solid was dissolved in water and washed with ether. The aqueous layer was acidified with concentrated hydrochloric acid and extracted with ethyl acetate. The organic layer was washed 5 times with saturated saline and dried over magnesium sulfate, followed by distillation under reduced pressure to evaporate the solvent to obtain the captioned compound as a colorless oil.

Yield 2.37 g Yield 97.3%; IR (liquid film method); ν max cm⁻¹:3452, 1729, 1647, 1601. NMR(90 MHz, CDCl3); δ:0.17–0.35(2H, m), 0.40–0.62(2H, m), 1.00(1H, m), 2.69 (2H, t, J=6.3 Hz), 3.34(2H, d, J=6.8 Hz), 3.40(0.5H, br s), 3.50(2H, t, J=6.3 Hz ), 3.91(3H, s), 13.8(0.5H, br s). Mass(EI); m/z:225(M⁺)

Reference Example 8
3-carboethoxy-1-cyclopropylmethyl-2,4-piperidinedione 8

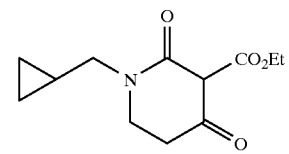

By the operation similar to Reference Example 6, the captioned compound was obtained as a colorless oil from 305 mg (13.26 mmol) of sodium metal, 10 ml of anhydrous ethanol, 3.15 g (11.05 mmol) of ethyl 3-(N-cyclopropylmethyl-N-carboethoxyacetamide) propionate 5, and 50 ml of anhydrous benzene.

Yield 2.59 g Yield 98%; IR (liquid film method); ν max cm⁻¹:1729, 1653. NMR(90 MHz, CDCl3); δ:0.17–0.36(2H, m), 0.40–0.62(2H, m), 1.02(1H, m) 1.40(3H, t, J=7.3 Hz), 2.67(2H, t, J=6.8 Hz), 3.34(2H, d, J=6.8 Hz), 3.50(2H, t, J=6.8 Hz), 3.60(0.3H, s), 4.38(2H, d, J=7.3 Hz), 14.0(0.7H, s). Mass(EI); m/z:239(M⁺)

Example 1
2-benzyl-8a-carboethoxy-1,6-dioxo-1,2,3,4,6,7,8,8a-octahydroisoquinoline 9

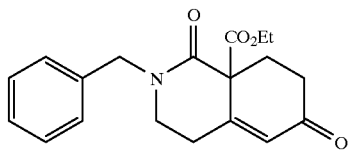

9

In 30 ml of anhydrous benzene and 15 ml of anhydrous tert-butanol, 8.73 g (31.75 mmol) of 1-benzyl-3-carboethoxy-2,4-piperidinedione 6 was dissolved and 428 mg (3.81 mmol) of potassium tert-butoxide was added thereto under argon stream, followed by heating the mixture to 70° C. for 2 hours. The mixture was then slowly cooled to room temperature and 4.44 ml (53.97 mmol) of methylvinylketone was added thereto dropwise. The mixture was then slowly heated to 80° C. and stirred for 5 hours. After the reaction, the mixture was cooled to room temperature and poured into a mixed solution of ether/ethyl acetate=9:1 and saturated aqueous ammonium chloride solution to carry out extraction. The organic layer was washed with saturated saline and dried over magnesium sulfate. The mixture was concentrated under reduced pressure to evaporate the organic solvent to obtain 9.64 g of a crude yellow oil.

To 38 ml of the solution of the obtained crude oil in anhydrous benzene, 4 ml (47.62 mmol) of pyrrolidine was added and the mixture was heated at 100° C. for 4 hours using a Dean-Stark's apparatus. After cooling the reaction solution, 15 ml of a mixture of acetic acid/water/sodium acetate=2:2:1 was added and the resulting mixture was heated at 100° C. for 3 hours. The reaction solution was poured into water and extracted with ethyl acetate. The organic layer was washed with 1N hydrochloric acid (×4), saturated aqueous sodium hydrogen carbonate solution and with saturated saline and dried over magnesium sulfate. The mixture was concentrated under reduced pressure to evaporate the organic solvent to obtain 5.8 g of a brown crude oil. The obtained product was subjected to chromatography (hexane/ethyl acetate=3:2) using 80 g of silica gel to obtain the captioned compound as a solid.

Yield 3.9 g, Yield 50%; mp. 72–74° C. (ether); IR (liquid film method); ν max cm⁻¹:1734, 1680, 1653, 1600. NMR(90 MHz, CDCl3); δ:1.29(3H, t, J=7.0 Hz), 3.28–3.47(2H, m), 4.26(2H, q, J=7.0 Hz), 4.34(1H, d, J=14.5 Hz), 4.97(1H, d, J=14.5 Hz), 5.98(1H, br s), 7.30(5H, s). Mass (EI); m/z:327 (M⁺)

Example 2
8a-carbomethoxy-2-cyclopropylmethyl-1,6-dioxo-1,2,3,4,6,7,8,8a-octahydroisoquinoline 10

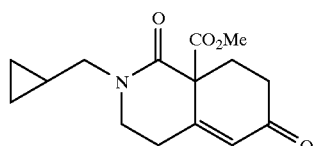

10

Operation 1

To a suspension containing 5 ml (0.125 mmol) of sodium hydride in 0.8 ml of benzene, a solution containing 300 mg (1.3 mmol) of 1-cyclopropylmethyl-3-carbomethoxy-2,4-piperidinedione 7 in 0.5 ml of benzene was added and the mixture was stirred at room temperature for 2 hours. Then a solution containing 0.1 ml (1.2 mmol) of methylvinylketone in 0.4 ml of benzene was added and the resulting mixture was stirred at 42° C. for 22 hours. Then 0.1 ml (1.2 mmol) of methylvinylketone was further added and 20 hours later, additional 0.05 ml (0.6 mmol) of methylvinylketone was added, followed by stirring the obtained mixture for 4 hours. The reaction solution was cooled to room temperature and distilled water and benzene were added thereto, thereby carrying out extraction. The organic layer was dried over anhydrous magnesium sulfate and the solvent was evaporated under reduced pressure to obtain 381 mg of crude oil.

The obtained oil was dissolved in 1.2 ml of benzene and 0.22 ml (2.6 mmol) of pyrrolidine was added. The obtained mixture was heated to reflux for 19 hours using Dean-Stark's apparatus and the generated water was removed by azeotropic distillation. The reaction mixture was cooled to room temperature and 1 ml of acetic acid/water/sodium acetate (2:2:1) was added, followed by heating the resulting mixture for 1.5 hours. After the reaction, dichloromethane and distilled water were added to carry out extraction. The obtained organic layer was washed with 1N hydrochloric acid, 1N sodium carbonate and with saturated saline, and dried over anhydrous magnesium sulfate. After filtration, the solvent was evaporated to obtain 310 mg of a crude oil. The obtained crude oil was subjected to column chromatography (chloroform) using 10 g of silica gel to obtain the captioned compound as a colorless solid.

Operation 2

To a solution containing 4 g (17.78 mmol) of Compound 7 in 20 ml of methanol, 115 mg (2.13 mmol) of sodium methoxide and then 3.65 ml (44.45 mmol) of methylvinylketone were added and the obtained mixture was stirred at room temperature for 10 hours. After the reaction, saturated aqueous ammonium chloride solution was added and the obtained mixture was poured to a mixed solution of ether/ethyl acetate (9:1 v/v)/saturated aqueous ammonium chloride solution, thereby carrying out extraction. The organic layer was washed with saturated saline and dried over anhydrous magnesium sulfate. After filtration, the solvent was evaporated under reduced pressure to obtain a crude oil.

The obtained oil was dissolved in 25 ml of benzene and 3.71 ml (44.45 mmol) of pyrrolidine was added. The obtained mixture was heated to reflux for 19 hours using Dean-Stark's apparatus and the generated water was removed by azeotropic distillation. The reaction mixture was cooled to room temperature and 20 ml of acetic acid/water/sodium acetate (2:2:1) was added, followed by heating the resulting mixture for 1.5 hours. After the reaction, ethyl acetate was added to carry out extraction. The obtained organic layer was washed with 1N hydrochloric acid, 1N sodium carbonate and with saturated saline, and dried over anhydrous magnesium sulfate. After filtration, the solvent was evaporated to obtain a crude oil. The obtained crude oil was subjected to column chromatography (hexane/ethyl acetate 3:4–1:2 v/v) using 17 g of silica gel to obtain the captioned compound as a colorless solid. The product was recrystallized from ether.

Operation 3

To a solution containing 300 mg (1.3 mmol) of Compound 7 in 1 ml of methanol, 0.13 ml (0.13 mmol) of 1N potassium hydroxide solution in methanol and 34 mg (0.13 mmol) of 18-crown-6 were added and the mixture was stirred at room temperature for 10 minutes. Methylvinylketone was added intermittently (0.1 ml (1.2 mmol), 0.1 ml (1.2 mmol), 0.05 ml (0.6 mmol)) and the resulting mixture was stirred for 22 hours. The reaction solution was concentrated under reduced pressure and the resultant was extracted with dichloromethane and saturated aqueous potassium chloride solution, followed by drying the organic layer over anhydrous sodium sulfate. The solvent was evaporated under reduced pressure to obtain 653 mg of a crude oil.

The obtained oil was dissolved in 10 ml of benzene and 0.2 ml (2.24 mmol) of pyrrolidine was added. The resulting mixture was heated to reflux for 6 hours using Dean-Stark's apparatus, and the generated water was removed by azeotropic distillation. The reaction mixture was then cooled to room temperature and 5 ml of acetic acid/water/sodium acetate (2:2:1) was added, followed by heating the mixture for 3 hours. After the reaction, dichloromethane and distilled water were added, thereby carrying out extraction. The obtained organic layer was washed with saturated sodium hydrogen carbonate solution and saturated saline, and dried over anhydrous magnesium sulfate. After filtration, the solvent was evaporated to obtain 634 mg of a crude oil. The obtained crude oil was subjected to column chromatography (ethyl acetate/hexane=1:1–2:1 v/v) using 18 g of silica gel to obtain the captioned compound as a colorless solid.

Yield Operation 1: 151 mg (42%), Operation 2: 3.55 gg (72%), Operation 3: 342 mg(95%) mp. 95.5–96.5° C. (ether) IR (liquid film method); ν max cm$^{-1}$:1744, 1680, 1657, 1628. NMR(90 MHz, CDCl3); δ:0.22–0.38(2H, m), 0.42–0.65(2H, m), 1.00(1H, m), 1.89–3.60(1 OH, m), 3.78 (3H, s), 5.98(1H, br s). Mass(EI); m/z:277(M$^+$); Elementary Analysis C$_{15}$H$_{19}$NO$_4$; Calcd. C, 64.97; H, 6.91; N, 5.05; Found C, 64.93; H, 6.91; N, 5.11

Example 3

8a-carboethoxy-2-cyclopropylmethyl-1,6-dioxo-1,2,3,4,6,7,8,8a-octahydroisoquinoline 11

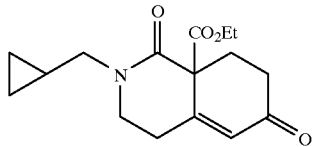

11

Operation 1

To a solution containing 6.25 g (26.15 mmol) of 1-cyclopropylmethyl-3-carboethoxy-2,4-piperidinedione 8 in 30 ml of ethanol, 213 mg (3.14 mmol) of sodium ethoxide and then 4.84 ml (58.84 mmol) of methylvinylketone were added and the mixture was stirred at room temperature for 7.5 hours. After the reaction, saturated aqueous ammonium chloride solution was added and the obtained mixture was poured into a mixed solution of ether/ethyl acetate (9:1 v/v)/saturated aqueous ammonium chloride solution, thereby carrying out extraction. The organic layer was washed with saturated ammonium chloride solution and dried over anhydrous magnesium sulfate. After filtration, the mixture was concentrated under reduced pressure to evaporate the solvent to obtain a crude oil.

The obtained oil was dissolved in 80 ml of benzene and 5.46 ml (65.38 mmol) of pyrrolidine was added and the resulting mixture was heated to reflux for 16 hours using Dean-Stark's apparatus, followed by removing the generated water by azeotropic distillation. The reaction mixture was then cooled to room temperature and 65 ml of acetic acid/water/sodium acetate (2:2:1 v/v/v) was added, followed by heating the resulting mixture for 1 hour. After the reaction, ethyl acetate was added and the obtained organic layer was washed with 1N hydrochloric acid, 1N sodium carbonate and with saturated saline and dried over anhydrous magnesium sulfate. After filtration, the solvent was evaporated to obtain a crude oil. The obtained crude oil was subjected to column chromatography (hexane/ethyl acetate 1:1–3:4 v/v) using 200 g of silica gel to obtain the captioned compound as a colorless solid.

Operation 2

In 2 ml of toluene, 200 mg (0.84 mmol) of 1-cyclopropylmethyl-3-carboethoxy-2,4-piperidinedione 8, 45 mg (0.17 mmol) of 18-crown-6 and 9.8 mg (0.17 mmol) of potassium fluoride was dissolved, and 0.14 ml (1.68 mmol) of methylvinylketone was added dropwise thereto, followed by stirring the mixture at room temperature for 8 hours. After the reaction, saturated aqueous ammonium chloride solution was added and the obtained mixture was poured into a mixed solvent of ether/ethyl acetate (9:1 v/v)/saturated aqueous ammonium chloride solution, thereby carrying out extraction. The organic layer was washed with saturated aqueous ammonium chloride solution and dried over anhydrous magnesium sulfate. After filtration, the mixture was concentrated under reduced pressure to evaporate the solvent to obtain a crude oil.

The obtained oil was dissolved in 10 ml of benzene and 0.18 ml (2.1 mmol) of pyrrolidine was added. The resulting mixture was heated to reflux for 16 hours using Dean-Stark's apparatus, followed by removing the generated water by azeotropic distillation. The reaction mixture was then cooled to room temperature and 0.25 ml of acetic acid/water/sodium acetate (2:2:1 v/v/v) was added, followed by heating the resulting mixture for 1 hour. After the reaction, ethyl acetate was added and the obtained organic layer was washed with 1N hydrochloric acid, 1N sodium carbonate and with saturated saline and dried over anhydrous magnesium sulfate. After filtration, the solvent was evaporated to obtain a crude oil. The obtained crude oil was subjected to column chromatography (hexane/ethyl acetate 1:1, 3:4 v/v) using 7 g of silica gel to obtain the captioned compound as a colorless solid.

Yield: Operation 1 5.34 g (70%) Operation 2 208 mg (85%) mp. 50–52° C. (ether); IR (liquid film method); ν max cm$^{-1}$:1740, 1680, 1653, 1628. NMR(90 MHz, CDCl3); δ:0.19–0.38(2H, m), 0.42–0.65(2H, m), 1.01(1H, m), 1.30 (3H, t, J=7.5 Hz), 1.91–3.65(10H, m), 4.25(2H, q, J=7.5 Hz), 6.00(1H, br s). Mass(EI); m/z:291(M$^+$); Elementary Analysis C$_{16}$H$_{21}$NO$_4$; Calcd. C, 65.96; H, 7.27; N, 4.81; Found C, 65.83; H, 7.11; N, 4.88

Example 4

2-benzyl-8a-carboethoxy-4a-phenyl-cis-1,6-dioxodecahydroisoquinoline 12

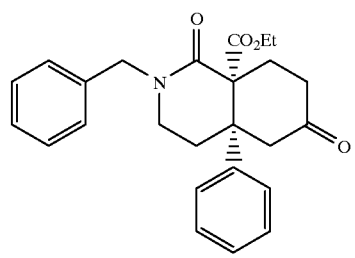

12

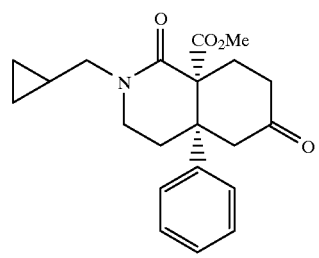

13

To 10 ml of a suspension containing 1.17 g (6.12 mmol) of cuprous iodide in ether, 12.3 ml (12.23 mmol) of a commercially available phenyllithium (1.0 M solution in cyclohexane/ether) was added dropwise under argon stream at 0° C. and the obtained mixture was stirred for 1 hour. To this mixture, 40 ml of a solution containing 1 g (3.06 mmol) of 2-benzyl-8a-carboethoxy-1,6-dioxo-1,2,3,4,6,7,8,8a-octahydroisoquinoline 9 obtained in Example 1 in ether was added dropwise and the resulting mixture was stirred at 0° C. for 1 hour and at room temperature for 1 hour. After the reaction, the reaction solution was diluted with 40 ml of saturated aqueous ammonium chloride solution and the resulting mixture was vigorously stirred for 30 minutes. The resultant was extracted with ethyl acetate. The aqueous layer was changed to alkaline condition with 80 ml of saturated aqueous ammonia and extracted with ethyl acetate. The organic layer was washed with saturated aqueous ammonia and saturated saline and dried over magnesium sulfate. The mixture was then concentrated under reduced pressure to evaporate the solvent to obtain 1.19 g of residue. The residue was recrystallized from ether/hexane to obtain 521 mg (42%) of the captioned compound as a pale yellow solid. Similarly, the obtained 1.19 g of residue was subjected to chromatography (hexane/ethyl acetate 2:1 and 1:2 v/v) using 35 g of silica gel to obtain 631 mg (51%) of the captioned compound as a white solid.

Yield 521 (42%) (recrystallization), 631 mg (51%) (chromatography); mp. 132–135° C. (ether/hexane); IR (KBr); ν max cm$^{-1}$:1729, 1630. NMR(400 MHz, CDCl3); δ:1.01(3H, t, J=7.2 Hz), 1.61(1H, dd, J=5.2 and 13.7 Hz), 2.20(1H, dt, J=4.3 and 14.1 Hz), 2.40(1H, dt, J=5.8 and 14.1 Hz), 2.52(1H, dm, J=16.5 Hz), 2.60(1H, d, J=16.2 Hz), 2.70(11H. dd, J=1.5 and 16.2 Hz), 2.78(1H, ddd, J=2.4, 5.8 and 14.1 Hz), 3.34(1H, ddd, J=7.0, 13.4 and 13.7 Hz), 3.45(1H, dt, J=5.2 and 13.4 Hz), 3.59(1H, dd, J=7.0 and 13.4 Hz), 3.87(1H, dq, J=7.2 and 10.5 Hz), 4.02(1H, dq, J=7.2 and 10.5 Hz), 4.54(1H, d, J=14.7 Hz), 4.94(1H, d, J=14.7 Hz), 7.21(2H, d, J=7.0 Hz), 7.22–7.33(6H, m), 7.36(2H, d, J=2.7 Hz). Mass(EI); m/z:405(M$^+$); Elementary Analysis $C_{25}H_{27}NO_4$; Calcd. C, 74.05; H, 6.71; N, 3.45; Found C, 74.06; H, 6.70; N, 3.62

Example 5

8a-carbomethoxy-2-cyclopropylmethyl-4a-phenyl-cis-1,6-dioxodecahydroisoquinoline 13

To 2 ml of a suspension containing 138 mg (0.72 mmol) of cuprous iodide in ether, 1.52 ml (1.44 mmol) of phenyllithium (1.0 M solution in cyclohexane/ether) was added dropwise at −20° C. under argon stream and the obtained mixture was stirred for 30 minutes. The reaction mixture was cooled to −75° C., and 0.183 ml (1.44 mmol) of chlorotrimethylsilane and then a solution containing 100 mg (0.36 mmol) of the 8a-carbomethoxy-2-cyclopropylmethyl-1,6-dioxo-1,2,3,4,6,7,8,8a-octahydroisoquinoline 10 obtained in Example 2 in 3 ml of THF/1.5 ml of ether were added dropwise. The reaction temperature was slowly raised to room temperature and the mixture was stirred for 2 hours. The reaction mixture was treated with 1N hydrochloric acid and the resultant was extracted with ethyl acetate. The organic layer was washed with saturated aqueous ammonium chloride solution and with saturated saline, and dried over magnesium sulfate. After filtration, the solvent was evaporated under reduced pressure to obtain a crude oil. The obtained oil was subjected to column chromatography (hexane/ethyl acetate 4:3) using 10 g of silica gel and recrystallized from ether/hexane to obtain the captioned compound as a white solid.

Yield: 40 mg Yield: 30%; mp. 76–80° C. (ether/hexane); IR (liquid film method); ν max cm$^{-1}$:1742, 1717, 1636, 1502, 1446. NMR(400 MHz, CDCl3); δ:0.30(1H, m), 0.34 (1H, m), 0.51–0.62(2H, m), 1.09(1H, m), 1.68(1H, dm), 2.14(1H, dt, J=3.4 and 14.2 Hz), 2.36(1H, dt, J=5.9 and 14.2 Hz), 2.50(1H, dm), 2.71(1H, ddd, J=3.4 5.9 and 13.9 Hz), 2.76(2H, br s), 3.23(1H, dd, J=6.8 and 14.2 Hz), 3.37(1H, dt, J=9.3 and 14.2 Hz), 3.47(3H, s), 3.63(1H, dd, J=6.8 and 13.9 Hz), 3.69–3.74(2H, m), 7.20–7.34(5H, m). HRMS $C_{21}H_{25}NO_4$; Calcd. 355.1784; Found 355.1783

Example 6

2-benzyl-8a-carboethoxy-4a-(m-methoxyphenyl)-cis-1,6-dioxodecahydroisoquinoline 14

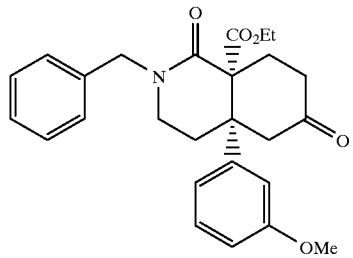

14

To a solution containing 115 mg (0.61 mmol) of m-bromoanisole in 1.5 ml of THF, 0.94 ml (1.2 mmol) of tert-butyllithium (1.3 M solution in pentane) was added dropwise at −70° C. under argon stream. The obtained suspension was warmed to −25° C. and THF was evaporated under reduced pressure using a vacuum pump. To the obtained residue, 1 ml of ether was added at −20° C. and the mixture was warmed to room temperature. The obtained red solution was added dropwise to 1 ml of a suspension containing 58.3 mg (0.31 mmol) of cuprous iodide in ether at 0° C. and the resulting mixture was stirred for 10 minutes. A solution containing 50 mg (0.15 mmol) of 2-benzyl-8a-carboethoxy-1,6-dioxo-1,2,3,4,6,7,8,8a-octahydroisoquinoline 9 obtained in Example 1 in 3 ml of ether was added dropwise to the mixture. After allowing to react at 0° C. to room temperature for 30 minutes, the mixture was treated with saturated aqueous ammonium chloride solution and then with 28% aqueous ammonia and the resultant was extracted with ethyl acetate. The organic layer was washed with saturated aqueous ammonium chloride solution and with saturated saline, and dried over magnesium sulfate. After filtration, the solvent was evaporated to obtain a crude oil. The obtained oil was subjected to chromatography (hexane/ethyl acetate 2:1, 4:3) using 10 g of silica gel and then recrystallized from ether/hexane (1:1) to obtain the captioned compound as a white solid.

Yield: 27 mg Yield: 40%; mp. 76–80° C. (ether/hexane); IR (liquid film method); ν max cm$^{-1}$:1738, 1715, 1642, 1607, 1584. NMR(400 MHz, CDCl3); δ:1.04(3H, t, J=7.9 Hz), 1.60(1H, dd, J=5.4 and 13.7 Hz), 2.21(1H, dt , J=5.4 and 14.9 Hz), 2.39(1H, dt, J=5.4 and 14.9 Hz), 2.52(1H, dm), 2.62(1H, d, J=16.1 Hz), 2.68(1H, dd, J=1.5 and 16.1 Hz), 2.78(1H, ddd, J=2.4 5.4 and 13.9 Hz), 3.31(1H, ddd, J=6.8 11.7 and 13.7 Hz), 3.44(1H , dt, J=5.4 and 11.7 Hz), 3.58(1H, dd, J=6.8 and 13.7 Hz), 3.76(3H, s), 3.93(1H, dq, J=7.3 and 10.7 Hz), 4.04(1H, dq, J=7.3 and 10.7 Hz), 4.54(1H, d, J=14. 7 Hz), 4.94(1H, d, J=14.7 Hz), 6.75–6.83 (3H, m), 7.21(1H, t, J=7.8 Hz), 7.28–7.40(5H, m). HRMS C$_{26}$H$_{29}$NO$_5$; Calcd. 435.2046; Found 435.2025

Example 7

8a-carboethoxy-2-cyclopropylmethyl-4a-(m-methoxyphenyl)-cis-1,6-dioxodecahydroisoquinoline 15

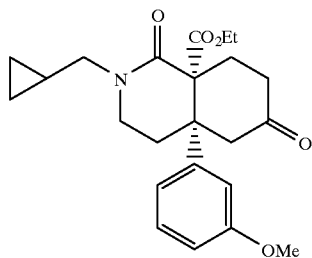

15

Operation 1

To a solution containing 0.7 ml (5.5 mmol) of m-bromoanisole in 15 ml of THF, 7.1 ml (11.0 mmol) of tert-butyllithium (1.55 M solution in pentane) was added dropwise at −70° C. under argon stream. The obtained suspension was warmed to −25° C. and THF was evaporated under reduced pressure using a vacuum pump. To the obtained residue, 10 ml of ether was added at −20° C. and the mixture was warmed to room temperature. The obtained red solution was added dropwise to 15 ml of a suspension containing 524 mg (2.75 mmol) of cuprous iodide in ether at 0° C. and the resulting mixture was stirred for 10 minutes. A solution containing 400 mg (1.38 mmol) of 8a-carboethoxy-2-cyclopropylmethyl-1,6-dioxo-1,2,3,4,6,7,8,8a-octahydroisoquinoline 11 obtained in Example 3 in 10 ml of ether was added dropwise to the mixture. After allowing to react at 0° C. to room temperature for 1 hour, the mixture was treated with saturated aqueous ammonium chloride solution and then with 28% aqueous ammonia and the resultant was extracted with ethyl acetate. The organic layer was washed with saturated aqueous ammonium chloride solution and with saturated saline, and dried over magnesium sulfate. After filtration, the solvent was evaporated to obtain a crude oil. The obtained oil was subjected to chromatography (hexane/ethyl acetate 3:2) using 41 g of silica gel to obtain the captioned compound as a colorless oil.

Operation 2

To a solution containing 1.03 g (5.5 mmol) of m-bromoanisole in 15 ml of diethyl ether, 7.2 ml (11.0 mmol) of tert-butyllithium (1.53 M solution in pentane) was added dropwise at −78° C. under argon stream. The obtained suspension was warmed to 0° C. and the mixture was added dropwise to 15 ml of a suspension containing 526 mg (2.76 mmol) of cuprous iodide in ether at 0° C., followed by stirring the resulting mixture at 0° C. for 10 minutes. Thereafter, a solution containing 400 mg (1.38 mmol) of 8a-carboethoxy-2-cyclopropylmethyl-1,6-dioxo-1,2,3,4,6,7,8,8a-octahydroisoquinoline 11 obtained in Example 3 in 10 ml of ether was added dropwise to the mixture. After allowing to react at 0° C. to room temperature for 2 hours, the mixture was treated with saturated aqueous ammonium chloride solution and then with 28% aqueous ammonia and the resultant was extracted with ethyl acetate. The organic layer was washed with saturated aqueous ammonium chloride solution and with saturated saline, and dried over anhydrous sodium sulfate. After filtration, the solvent was evaporated to obtain a crude oil. The obtained oil was subjected to chromatography (hexane/ethyl acetate 3:2) using 40 g of silica gel to obtain the captioned compound as a colorless oil.

Operation 3

To a mixed solution of 97 mg (4 mmol) of magnesium and 1 ml of THF, 0.41 ml (3.3 mmol) of m-bromoanisole was added dropwise under refluxing condition to dissolve the magnesium. A mixed solution containing 190 mg (1.51 mmol) of manganese (II) chloride, 348 mg (8.21 mmol) of lithium chloride, 149 mg (1.51 mmol) of cuprous chloride, and 400 mg (1.38 mmol) of 8a-carboethoxy-2-cyclopropylmethyl-1,6-dioxo-1,2,3,4,6,7,8,8a-octahydroisoquinoline 11 in 2 ml of THF was separately prepared. To this solution, the above-mentioned m-anisilmagnesium bromide solution in THF was added dropwise at 0° C. under stirring. The reaction solution was warmed to room temperature and the mixture was allowed to react for 2 hours. The reaction mixture was again cooled in ice and 10 ml of 1N hydrochloric acid was added, followed by extraction with ethyl acetate. The ethyl acetate layer was washed with 28% aqueous ammonia/saturated aqueous ammonium chloride solution (1:1 v/v), saturated aqueous sodium hydrogen carbonate and then with saturated saline, and dried over anhydrous sodium sulfate. After filtration, the solvent was evaporated to obtain a crude oil. The obtained oil was subjected to chromatography (hexane/ethyl acetate 3:2) using 40 g of silica gel to obtain the captioned compound as a colorless oil.

Operation 4

To the reaction system same as in Operation 3, 0.52 ml (4.1 mmol) of trimethylsilyl chloride was added and then the m-anisilmagnesium bromide solution in THF same as in Operation 3 was added dropwise at 0° C. under stirring. The reaction solution was warmed to room temperature and the mixture was allowed to react for 1 hour. The post treatment and purification as in Operation 3 were carried out to obtain the captioned compound as a colorless oil.

Operation 5

The same operation as in Operation 3 was repeated except that dimethoxymethane was used in place of THF solvent for preparation of m-anisylmagnesium bromide and 1,4-conjugate addition reaction. The post treatment and purification as in Operation 3 were carried out to obtain the captioned compound as a colorless oil.

Operation 1 Yield 274 mg (50%)
Operation 2 Yield 219 mg (40%)
Operation 3 Yield 192 mg (35%)
Operation 4 Yield 219 mg (40%)
Operation 5 Yield 164 mg (30%)

IR (liquid film method); ν max cm$^{-1}$:2964, 1738, 1715, 1634, 1607, 1584, 1493, 1448. NMR(400 MHz, CDCl3); δ:0.26–0.38(2H, m), 0.51–0.62(2H, m), 1.04 and 1.26(3H, each t, each J=7.3 Hz), 1.18(1H, m), 1.68(2H, dd, J=4.4 and 13.2 Hz), 2.18(1H, dt, J=4.4 and 13.7 Hz), 2.36(1H, dt, J=5.9 and 14.2 Hz), 2.48(1H, br d, J=15.6 Hz), 2.74(2H, s), 3.29(1H, dd, J=6.8 and 13.7 Hz), 3.36(1H, m), 3.54(1H, dd, J=7.3 and 13.7 Hz), 3.63–3.76(2H, m), 3.77(3H, s), 3.89, 3.91, 3.99, and 4.02(2H, each q, each J=7.3 Hz), 6.80–6.82 (3H, m), 7.22(1H, t, J=7.3 Hz). HRMS $C_{23}H_{29}NO_5$; Calcd. 399.2046; Found 399.2033

Example 8
2-benzyl-8a-carboethoxy-6,6-ethylenedioxy-4a-phenyl-cis-1-oxodecahydroisoquinoline 16

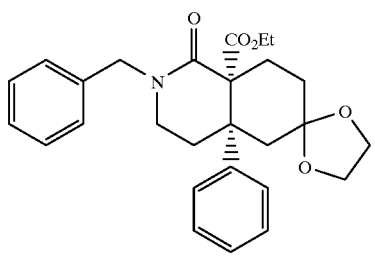

16

A solution containing 117 mg (0.29 mmol) of 2-benzyl-8-carboethoxy-4a-phenyl-cis-1,6-dioxodecahydroisoquinoline 12, 52 μl (0.86 mmol) of ethylene glycol and 11 mg (0.06 mmol) of p-toluenesulfonic acid in 4 ml of benzene was heated at 110° C. for 2 hours using a Dean-Stark's apparatus. After the reaction, the mixture was diluted with ethyl acetate and the resultant was washed with saturated aqueous sodium hydrogen carbonate solution and with saturated saline, followed by drying the resultant over magnesium sulfate. The product was concentrated under reduced pressure and the obtained residue was subjected to column chromatography (hexane/ethyl acetate 1:1) using 8 g of silica gel to obtain the captioned compound as a colorless oil.

Yield 104 mg, Yield 80%; mp. 76–80° C. (ether/hexane); IR (liquid film method); ν max cm$^{-1}$:1725, 1638, 1499, 1448. NMR(400 MHz, CDCl3) δ:1.03(3H, t, J=7.3 Hz), 1.64(1H, m), 1.83(1H, m), 2.20(2H, d, J=2.9 Hz), 2.49(1H, m), 2.65(2H, m), 3.24(1H, m), 3.38(1H, m), 3.82–3.99(6H, m), 4.45(1H, d, J=14.7 Hz), 4.87(1H, d, J=14.7 Hz), 7.16–7.36(8H, m), 7.54(2H, d, J=7.8 Hz). Mass(EI); m/z:449(M$^+$)

Example 9
8a-carboethoxy-2-cyclopropylmethyl-6,6-ethylenedioxy-4a-(m-methoxyphenyl)-cis-1-oxodecahydroisoquinline 17

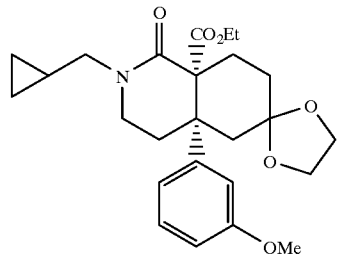

17

By the operation similar to Example 8, the captioned compound was obtained as a colorless oil from 90 mg of 8a-carboethoxy-2-cyclopropylmethyl-4a-(m-methoxyphenyl)-cis-1,6-dioxodecahydroisoquinoline 15, 0.07 ml of ethylene glycol and a catalytic amount of p-toluenesulfonic acid.

Yield: 72 mg, Yield: 72%; IR (liquid film method); ν max cm$^{-1}$:2938, 1730, 1636, 1584, 1495. NMR(400 MHz, CDCl3); δ:0.21–0.36(2H, m), 0.46–0.59(2H, m), 0.96 and 1.05(3H, each t, each J=7.3 Hz), 1.06(1H, m), 1.56(1H, m), 1.81(1H, m), 2.11(1H, m), 2.21(2H, s), 2.43(1H, m), 2.60 (1H, m), 2.77(1H, m), 3.28–3.42(2H, m), 3.43(1H, m), 3.58(1H, m), 3.78 and 3.79(3H, each s), 3.86–4.02(6H, m), 6.74(1H, dd, J=2.0 and 7.8 Hz), 7.07(1H, dd, J=2.0 and 7.8 Hz), 7.17(1H, t, J=7.8 Hz), 7.32(1H, t, J=2.0 Hz). HRMS $C_{25}H_{33}NO_6$; Calcd. 443.2308; Found 443.2330

Example 10
2-benzyl-6,6-ethylenedioxy-4a-phenyl-1-oxodecahydroisoquinoline 18

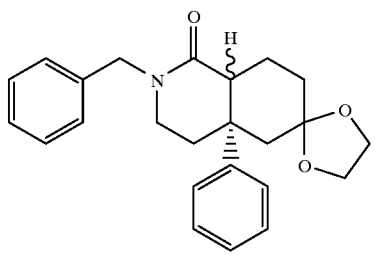

18

To a suspension containing 170 mg (4.25 mmol) of sodium hydride in 7 ml of dimethylformamide, 0.58 ml (7.79 mmol) of ethanethiol was added dropwise under argon stream. After generation of hydrogen gas had ceased, a solution containing 318 mg (0.71 mmol) of 2-benzyl-8a-carboethoxy-6,6-ethylenedioxy-4a-phenyl-cis-1-oxodecahydroisoquinoline 16 obtained in Example 8 in 5 ml of dimethylformamide was added and the mixture was heated at 80° C. for 6 hours under stirring. After the reaction, the mixture was concentrated under reduced pressure at a temperature not higher than 50° C. to evaporate the solvent and the obtained residue was diluted with ethyl acetate. The resultant was washed with saturated aqueous ammonium chloride solution and with saturated saline and dried over magnesium sulfate. The solvent was evaporated and the obtained residue was subjected to column chromatography (hexane/ethyl acetate 2:1, 1:1, 1:2) using 12 g of silica gel to obtain the captioned compound as a mixture of trans/cis isomers (trans/cis 8:1). The mixture was a colorless solid and recrystallized from ether/hexane to obtain pure trans isomer.

Yield: 245 mg Yield: 95.2%; Trans Isomer; mp. 148–150° C. (ether/hexane); IR (KBr); ν max cm$^{-1}$:1634, 1495, 1452. NMR(400 MHz, CDCl3); δ:1.68(2H, d, J=13.2 Hz), 1.84–1.97(3H, m), 2.10(1H, m), 2.40–2.61(4H, m), 2.99(1H, m), 3.49(1H, dt, J=6.8 and 8.3 Hz), 3.61(1H, ddd, J=5.4 6.8 and 8.3 Hz), 3.79(1H, dd, J=6.8 and 14.2 Hz), 3.85(1H, m), 4.24(1H, d, J=14.7 Hz), 4.71(1H, d, J=14.7 Hz), 7.12–7.32 (10H, m). Mass(EI); m/z:377(M$^+$); Elementary Analysis C$_{24}$H$_{27}$NO$_3$; Calcd. C, 76.37; H, 7.21; N, 3.71; Found C, 76.24; H, 7.27; N, 3.64; Cis Isomer; NMR (400 MHz, CDCl3); δ:1.55–1.70(2H, m), 1.80–2.10(5H, m), 2.36–2.55 (3H, m), 2.82(1H, m), 2.94(1H, m), 3.90–3.94(2H, m), 3.97–4.04(2H, m), 4.29(1H, d, J=14.7 Hz), 4.58(1H, d, J=14.7 Hz), 7.00(2H, m), 7.15–7.34(8H, m).

Example 11

2-cyclopropylmethyl-6,6-ethylenedioxy-4a-(m-methoxyphenyl)-1-oxodecahydroisoquinoline 19

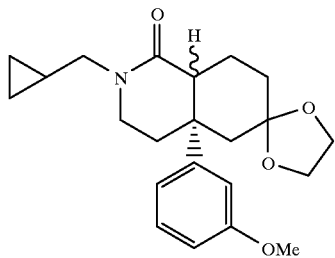

19

By the operation similar to Example 10, the captioned compound was obtained as a trans/cis mixture (8:1) (colorless oil) from sodium hydride (22.6 mg), ethanethiol (0.08 ml), 8a-carboethoxy-2-cyclopropylmethyl-6,6-ethylenedioxy-4a-(m-methoxyphenyl)-cis-1-oxodecahydroisoquinoline 17(50 mg).

Yield: 40 mg, Yield 95%; IR (liquid film method); ν max cm$^{-1}$:2956, 1634, 1584, 1491, 1452, 1435. NMR (400 MHz, CDCl3); δ:0.11(1H, m), 0.21(1H, m), 0.30–0.46(2H, m), 0.84(1H, m), 1.64(1H, m), 1.84(1H, m), 1.97–2.03(2H, m), 2.10(1H, dq, J=3.9 and 13.2 Hz), 2.36(1H, dd, J=3.2 and 12.5 Hz), 2.51(1H, d, J=2.4 Hz), 2.55(1H, d, J=2.4 Hz), 2.70(1H, m), 2.99(1H, dd, J=6.8 and 13.7 Hz), 3.11(1H, m), 3.32(2H, dd, J=6.8 and 13.7 Hz), 3.55(1H, t, J=6.8 Hz), 3.65(1H, m), 3.77(3H, s, trans-OMe), 3.81(1H, m), 3.87(1H, m), 4.00(0.37H, s, cis-OMe), 6.72(1H, dd, J=2.4 and 8.3 Hz), 6.80(1H, t, J=2.4 Hz), 6.82(1H, d, J=8.3 Hz), 7.18(1H, t, J=8.3 Hz). Mass(EI); m/z:371(M$^+$)

Reference Example 9

2-benzyl-6,6-ethylenedioxy-4a-phenyl-2,3,4,4a,5,6,7,8-octahydroisoquinoline 20

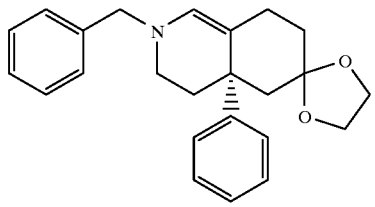

20

To a solution containing 52 mg (0.14 mmol) of 2-benzyl-6,6-ethylenedioxy-4a-phenyl-1-oxodecahydroisoquinoline 18 in 1.5 ml of tetrahydrofuran, 0.81 ml (0.73 mmol) of a 0.9M solution of diisobutylaluminum hydride in hexane was added dropwise at 0° C. The reaction solution was stirred at room temperature for 30 minutes and 3 ml of methanol was carefully added, followed by stirring the resulting mixture for 20 minutes. The mixture was concentrated under reduced pressure to evaporate the solvent and the obtained residue was added to a mixed solution of 10 ml of 3N aqueous sodium hydroxide solution and 20 ml of chloroform, thereby carrying out extraction. The aqueous layer was additionally extracted twice with chloroform. The organic layer was washed with saturated saline and dried over sodium sulfate. The product was concentrated under reduced pressure to obtain 42.5 mg (85.3%) of the captioned compound as a crude oil.

IR (liquid film method); ν max cm$^{-1}$:1659, 1493, 1448

Reference Example 10

2-cyclopropylmethyl-6,6-ethylenedioxy-4a-(m-methoxyphenyl)-2,3,4,4a,5,6,7,8-octahydroisoquinoline 21

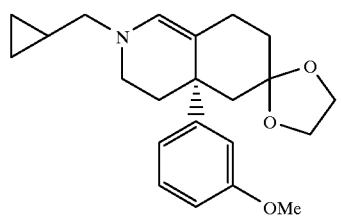

21

To a solution containing 13 mg (0.035 mmol) of 2-cyclopropylmethyl-6,6-ethylenedioxy-4a-(m-methoxyphenyl)-1-oxodecahydroisoquinoline 19 in 0.5 ml of tetrahydrofuran, 0.2 ml (0.2 mmol) of a 0.9M solution of diisobutylaluminum hydride in hexane was added dropwise at 0° C. The reaction solution was stirred at 0° C. for 15 minutes and the reaction solution was warmed to room temperature, followed by stirring the mixture for another 30 minutes. Then 3 ml of methanol was added and the resulting mixture was stirred for 15 minutes. The mixture was concentrated under reduced pressure to evaporate the solvent and the obtained residue was added to a mixed solution of 4 ml of 3N aqueous sodium hydroxide solution and 10 ml of chloroform, thereby carrying out extraction. The aqueous layer was additionally extracted twice with chloroform. The organic layer was washed with saturated saline and dried over sodium sulfate. The product was concentrated under reduced pressure to obtain the captioned compound as a pale yellow crude oil.

IR (liquid film method); ν max cm$^{-1}$:2930, 1659, 1605, 1582, 1487. NMR(90 MHz, CDCl3); δ:0.02–0.17(2H, m), 0.39–0.60(2H, m), 0.91(1H, m), 1.51–2.80(12H, m), 3.55–3.94(4H, m), 3.80(3H, s), 4.09(1H br s), 6.70(1H, m), 6.92–7.32(3H, m). Mass (EI); m/z:355(M$^+$)

Example 12

2-benzyl-6,6-ethylenedioxy-4a-phenyl-trans-decahydroisoquinoline 22

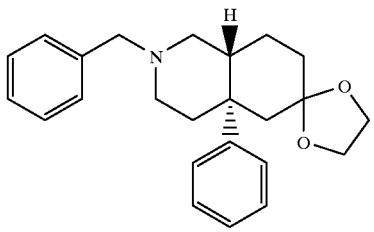

The enamine intermediate 20 obtained in Reference Example 9 was dissolved in 2 ml of methanol and 26 mg (0.41 mmol) of sodium cyanoborohydride was added at −10° C. To this mixture, two drops of methanol saturated with hydrochloric acid were added under stirring and the resulting mixture was stirred for 30 minutes keeping the pH at about 4. The reaction solution was concentrated under reduced pressure and the obtained residue was dissolved in chloroform. The resulting mixture was washed with saturated aqueous sodium hydrogen carbonate solution and with saturated saline, and dried over magnesium sulfate. The solvent was evaporated and the obtained residue was subjected to chromatography (chloroform/methanol 60/1) using 5 g of silica gel to obtain the captioned compound as a colorless oil. Yield: 37 mg, Total yield from Reference Example 9: 74.3%

IR (liquid film method); ν max $cm^{-1}$:1497, 1448. NMR (400 MHz, CDCl3); δ:1.57–1.64(2H, m), 1.69–1.80(4H, m), 1.98–2.07(2H, m), 2.27(1H, dq, J=4.9 and 13.2 Hz), 2.39 (1H, dd, J=2.4 and 13.7 Hz), 2.54(1H, m), 2.75–2.88(2H, m), 3.30(1H, dd, J=7.3 and 15.1 Hz), 3.40–3.50(1H, m), 3.52(1H, m), 3.73(1H, dd, J=7.3 and 14.2 Hz), 3.81(1H, dt, J=4.9 and 7.3 Hz), 7.13(1H, t, J=7.3 Hz), 7.24–7.32(7H, m), 7.41(2H, d, J=7.3 Hz). Mass (EI); m/z:363($M^+$)

Example 13
2-cyclopropylmethyl-6,6-ethylenedioxy-4a-(m-methoxyphenyl)-trans-decahydroisoquinoline 23

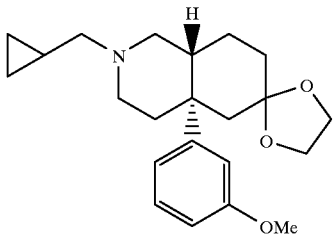

The enamine intermediate 2 obtained in Reference Example 10 was dissolved in 0.5 ml of methanol, and 6.6 mg (0.105 mmol) of sodium cyanoborohydride was added at 0° C. To this mixture, three drops of methanol saturated with hydrochloric acid were added under stirring and the resulting mixture was stirred for 15 minutes keeping the pH at about 3–4. The reaction solution was concentrated under reduced pressure and the obtained residue was dissolved in chloroform. The resulting mixture was washed with saturated aqueous sodium hydrogen carbonate solution and with saturated saline, and dried over magnesium sulfate. The solvent was evaporated and the obtained residue was subjected to chromatography (chloroform/methanol 10/1) using 4 g of silica gel to obtain the captioned compound as a colorless oil. Yield: 10 mg, Total yield from Reference Example 10: 80%

IR (liquid film method); ν max $cm^{-1}$:2934, 1607, 1582, 1491, 1458. NMR(400 MHz, CDCl3); δ:0.02–0.11(2H, m), 0.43–0.52(2H, m), 0.78–0.88(1H, m), 1.56(1H, d, J=13.7 Hz), 1.63–1.73(1H, m), 1.73–1.83(4H, m), 1.98–2.08(2H, m), 2.17(1H, dd, J=6.6 and 12.5 Hz), 2.23–2.36(2H, m), 2.39(1H, dd, J=2.2 and 13.5 Hz), 2.71–2.76(1H, m), 2.79 (1H, dd, J=12.0 and 12.0 Hz), 2.95(1H, br dd, J=3.4 and 11.2 Hz), 3.36(1H, ddd, J=7.3, 7.3 and 7.8 Hz), 3.57(1H, ddd, J=5.4, 6.8 and 7.8 Hz), 3.75(1H, ddd, J=6.8, 7.3 and 7.3 Hz), 3.80(3H, s), 3.82(1H, ddd, J=5.4, 7.3 and 7.3 Hz), 6.66(1H, dd, J=2.2 and 8.1 Hz), 6.97(1H, br s), 7.02(1H, br d, J=8.1 Hz), 7.19(1H, dd, J=8.1 and 8.1 Hz). HRMS $C_{22}H_{31}NO_3$; Calcd. 357.2304; Found 357.2302

Reference Example 11
2-benzyl-4a-phenyl-trans-6-oxodecahydroisoquinoline 24

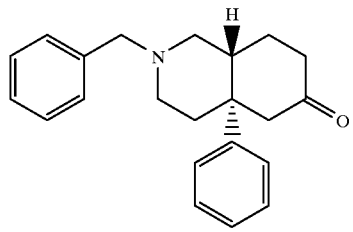

In 4.5 ml of 1N sulfuric acid, 57 mg (0.16 mmol) of 2-benzyl-6,6-ethylenedioxy-4a-phenyl-trans-decahydroisoquinoline 22 obtained in Example 12 was dissolved and the obtained solution was stirred at 25° C. for 24 hours. The reaction solution was changed to alkaline condition with 5% aqueous sodium hydroxide solution and the resultant was extracted three times with chloroform. The organic layer was washed with saturated saline and dried over magnesium sulfate. The mixture was concentrated under reduced pressure to evaporate the solvent to obtain sufficiently pure captioned compound as an oil.

Yield: 51 mg, Yield: 100%; IR (liquid film method); ν max $cm^{-1}$:1713. NMR(400 MHz, CDCl3); δ:1.89–2.00(3H, m), 2.03(1H, m), 2.23–2.56(5H, m), 2.63(1H, m), 2.72(1H, t, J=11.5 Hz), 2.87(1H, dd, J=3.4 and 11.5 Hz), 2.95(1H, dd, J=1.5 and 13.7 Hz), 3.53(2H, s), 7.17(1H, t, J=7.3 Hz), 7.27–7.34(7H, m), 7.41(2H, d, J=7.3 Hz). Mass (EI); m/z:319($M^+$)

Reference Example 12
2-cyclopropylmethyl-4a-(m-methoxyphenyl)-trans-6-oxodecahydroisoquinoline 25

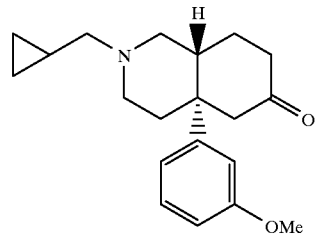

By the operation similar to Reference Example 11, the captioned compound was obtained from 10 mg (0.028 mmol) of 2-cyclopropylmethyl-6,6-ethylenedioxy-4a-(m-methoxyphenyl)-trans-decahydroisoquinoline 23 and 1 ml of 1N sulfuric acid.

Yield: 7.5 mg, Yield: 85.6%; IR (liquid film method); ν max cm$^{-1}$:2934, 1717, 1605, 1582. NMR(400 MHz, CDCl3); δ:0.05–0.11(2H, m), 0.47–0.53(2H, m), 0.89(1H, m), 1.90–2.07(4H,m), 2.19–2.44(6H, m), 2.56(1H, m), 2.74 (1H, t, J=11.7 Hz), 2.84(1H,dd, J=1.5 and 14.2 Hz), 2.91 (1H, m), 3.11(1H, br dd), 3.71(3H, s), 6.65(1H, m), 6.87–6.92(2H, m), 7.15(1H, t, J=8.3 Hz). HRMS $C_{20}H_{27}NO_2$; Calcd. 313.2042; Found 313.2061

Example 14

2-cyclopropylmethyl-6,6-ethylenedioxy-4a-(m-hydroxyphenyl)-trans-decahydroisoquinoline 26

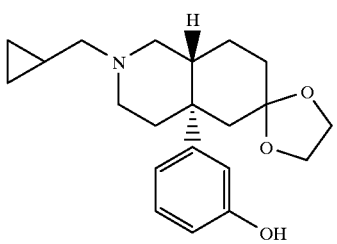

Under argon stream, 916 mg (2.56 mmol) of 2-cyclopropylmethyl-6,6-ethylenedioxy-4a-(m-methoxyphenyl)-trans-decahydroisoquinoline 23 obtained in Example 13 was dissolved in 20 ml of anhydrous dimethylformamide, and 1.16 ml (12.8 mmol) of 1-propanethiol and 865 mg (7.71 mmol) of potassium tert-butoxide were added and the resulting mixture was stirred at 150° C. for 7 hours. After cooling the mixture to room temperature, the solvent was evaporated under reduced pressure. To the residue, 25 ml of saturated aqueous sodium hydrogen carbonate solution was added and the resultant was extracted three times with 25 ml of chloroform/ethanol (3:1). The organic layer was dried over anhydrous sodium sulfate and concentrated to obtain 792 mg (90%) of the captioned compound as a crude crystal. Needle-shaped crystals were obtained by recrystallization from methanol.

Yield: 547 mg Yield: 62%; mp. 197.5–199.0 ° C. (methanol); IR (KBr); ν max cm$^{-1}$:3400, 3028, 1620, 1580, 1499, 1367, 1274, 1089, 913, 777. NMR(400 MHz, CDCl3); δ:0.02–0.11(2H, m), 0.43–0.51(2H, m), 0.81–0.89(1H, m), 1.55(1H, d, J=13.4 Hz), 1.60–1.90(1H, br s, OH), 1.63–1.68 (1H, m), 1.68–1.83(4H, m), 1.97–2.08(2H, m), 2.20(1H, dd, J=6.7 and 12.5 Hz), 2.24–2.34(2H, m), 2.35(1H, dd, J=2.3 and 13.6 Hz), 2.73–2.77(1H, m), 2.81(1H, dd, J=1.9 and 11.9 Hz), 2.97(1H, br dd, J=3.3 and 11.3 Hz), 3.38(1H, ddd, J=7.0, 7.3 and 7.6 Hz), 3.58(1H, ddd, J=5.2, 7.0 and 7.6 Hz), 3.75(1H, ddd, J=7.0, 7.0 and 7.0 Hz), 3.81(1H, ddd, J=5.2, 7.0 and 7.3 Hz), 6.57(1H,dd, J=2.1 and 7.9 Hz), 6.88(1H, br s), 6.94(1H, br d, J=7.9 Hz), 7.12(1H, dd, J=7.9 and 7.9 Hz). Mass(EI); m/z:343(M$^+$); Elementary Analysis $C_{21}H_{29}NO_3$; Calcd. C, 73.44; H, 8.51; N, 4.04; Found C, 73.26; H, 8.44; N, 4.13

Example 15

2-cyclopropylmethyl-4a-(m-hydroxyphenyl)-trans-6-oxodecahydroisoquinoline 27

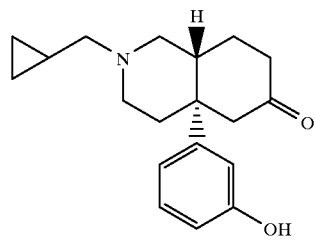

In 7.5 ml of 1,4-dioxane, 508 mg (1.48 mmol) of 2-cyclopropylmethyl-6,6-ethylenedioxy-4a-(m-hydroxyphenyl)-trans-decahydroisoquinoline 26 obtained in Example 14 was dissolved and 2.5 ml of 3N hydrochloric acid was added thereto, followed by stirring the mixture at room temperature for 40 minutes. To the mixture, 30 ml of saturated aqueous sodium hydrogen carbonate solution was added and the resultant was extracted three times with 30 ml of chloroform/ethanol (3:1). The organic layer was dried over anhydrous sodium sulfate and the resultant was concentrated. The obtained 495 mg of crude crystals were recrystallized twice from methanol/ethyl acetate to obtain the captioned compound as needle-shapecd crystals.

Yield: 346 mg, Yield: 78%; mp. 201.5–204.0 ° C. (methanol/ethyl acetate); IR (KBr); ν max cm$^{-1}$:3400, 3082, 1711, 1584, 1491, 1354, 1232, 1214, 1056, 874, 791, 731. NMR(400 MHz, CDCl3); δ:0.07–0.14(2H, m), 0.47–0.55 (2H, m), 0.83–0.93(1H, m), 1.92– 2.08(4H, m), 2.27–2.59 (7H, m), 2.72(1H, dd, J=11.7 and 11.7 Hz), 2.85–2.93(2H, m), 3.07(1H, br dd, J=3.9 and 11.7 Hz), 3.20–4.50(1H,br s, OH), 6.61(1H, dd, J=2.0 and 7.8 Hz), 6.88(1H, br s), 6.95(1H, br d, J=7.8 Hz), 7.12(1H, dd, J=7.8 and 7.8 Hz). Mass(EI); m/z:299(M$^+$); Elementary Analysis $C_{19}H_{25}NO_2$.0.1 $H_2O$; Calcd. C, 75.76; H, 8.48; N, 4.65; Found C, 75.67; H, 8.38; N, 4.68; $C_{19}H_{25}NO_2$.HCl. 0.4 $H_2O$; Calcd. C, 66.52; H, 7.87; N, 4.04; C 1, 10.33; Found C, 66.30; H, 7.80; N, 4.06; C 1, 10.07

INDUSTRIAL AVAILABILITY

By the present invention, a novel short process for synthesizing 4a-aryl-trans-6-oxodecahydroisoquinolines was established and the present invention may be utilized for development of analgesics and/or narcotic antagonists, and immunosuppressive agents.

We claim:

1. A process for producing 4a-aryl-trans-6-oxodecahydroisoquinoline compounds comprising:

reacting a compound of the formula (I)

(I)

wherein R$^1$ is $C_1$–$C_6$ alkyl, allyl, benzyl, phenethyl or $C_4$–$C_7$ cycloalkylalkyl and R$^2$ is $C_1$–$C_4$ alkyl or benzyl, with methylvinylketone to convert the compound of the formula (I) to a compound of the formula (II)

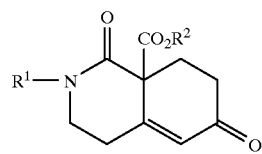
(II)

wherein $R^1$ and $R^2$ represent the same meanings as described above;

reacting the compound of the formula (II) with an aromatic metal compound prepared from a compound of the formula (III)

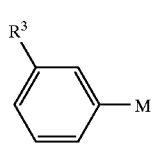
(III)

wherein $R^3$ is a hydrogen atom, $C_1$–$C_4$ alkoxy or benzyloxy, M is lithium, magnesium chloride, magnesium bromide or magnesium iodide, and a metal compound, the metal of which is selected from the group of metals belonging to Group VIIB, VIII, IB, IIB and IIIA metals, to convert the compound (II) to a compound of the formula (IV)

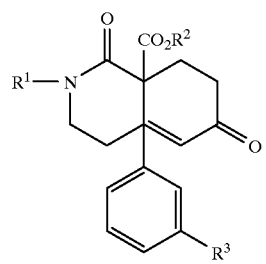
(IV)

wherein $R^1$, $R^2$ and $R^3$ are defined as above;

reacting the compound of the formula (IV) with an alcohol, to convert the compound of the formula (IV) to a compound of the formula (V)

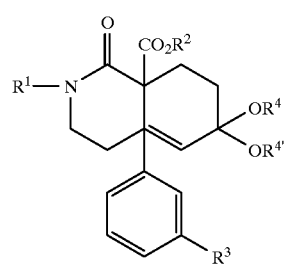
(V)

wherein $R^1$, $R^2$ and $R^3$ are defined as above, $R^4$ and $R^{4'}$ independently are methyl or ethyl, or $R^4$ and $R^{4'}$ are bonded to form ethylene or trimethylene;

decarboxylating the compound of the formula (V), to convert the compound of the formula (V) to a compound of the formula (VI)

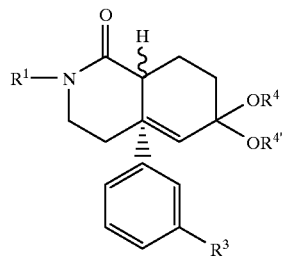
(VI)

wherein $R^1$, $R^3$, $R^4$ and $R^{4'}$ are defined as above;

reducing the compound of the formula (VI) to a compound of the formula (VII)

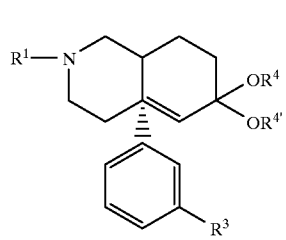
(VII)

wherein $R^1$, $R^3$, $R^4$ and $R^{4'}$ are defined as above; and reducing the compound of the formula VII to a compound of the formula (VIII)

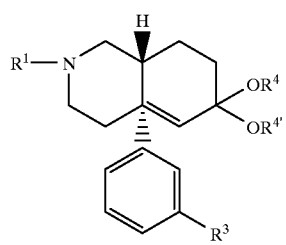
(VIII)

wherein $R^1$, $R^3$, $R^4$ and $R^{4'}$ are defined as above; and hydrolyzing the compound of the formula (VIII) to obtain a compound of the formula (IX)

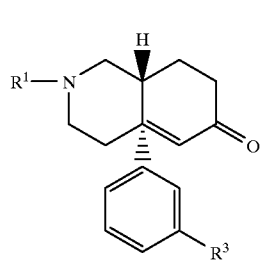
(IX)

wherein $R^1$ and $R^3$ are defined as above.

2. A process for producing 4a-aryl-trans-6-oxodecahydroisoquinoline compounds comprising:

reacting a compound of the formula (I)

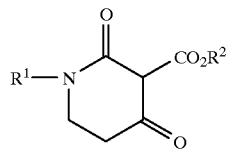
(I)

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, with methylvinylketone to convert the compound of the formula (I) to a compound of the formula (II)

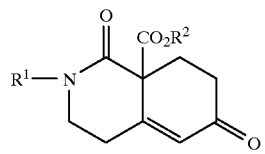
(II)

wherein $R^1$ and $R^2$ are defined as above;

reacting the compound of the formula (II) with an aromatic metal compound prepared from a compound of the formula (III)

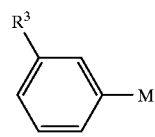
(III)

wherein $R^3$ is $C_1$–$C_4$ alkoxy or benzyloxy, M is lithium, magnesium chloride, magnesium bromide or magnesium iodide, and a metal compound, the metal of which is selected from the group of metals belonging to Groups VIIB, BIII, IB, IIB and IIIA, to convert the compound (II) to a compound of the formula (IV)

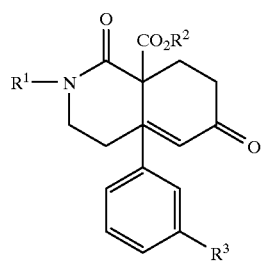
(IV)

wherein $R^1$, $R^2$ and $R^3$ are defined as above;

reacting the compound of the formula (IV) with an alcohol to convert the compound of the formula (IV) to a compound of the formula (V)

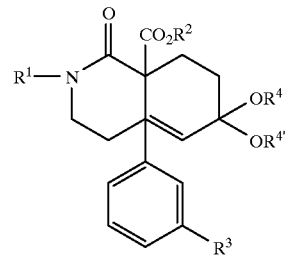
(V)

wherein $R^1$, $R^2$ and $R^3$ are defined as above, $R^4$ and $R^{4'}$ independently are methyl or ethyl, or $R^4$ and $R^{4'}$ are bonded to form ethylene or trimethylene;

decarboxylating the compound of the formula (V), to convert the compound of the formula (V) to a compound of the formula (VI)

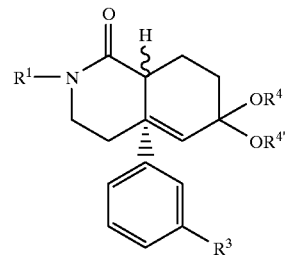
(VI)

wherein $R^1$, $R^3$, $R^4$ and $R^{4'}$ are defined as above;

reducing the compound of the formula (VI) to a compound of the formula (VII)

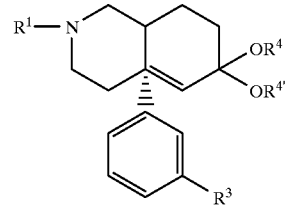
(VII)

wherein $R^1$, $R^3$, $R^4$ and $R^{4'}$ are defined as above;

reducing the compound of the formula (VII) to a compound of the formula (VIII)

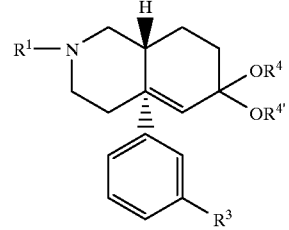
(VIII)

wherein $R^1$, $R^3$, $R^4$ and $R^{4'}$ are defined as above;

cleaving the phenol ether bond of the compound of the formula (VIII), thereby converting the compound of the formula (VIII) to the compound of the formula (X)

(X)

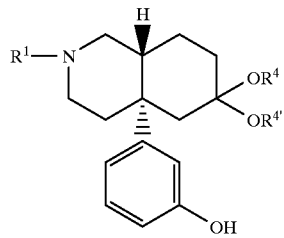

wherein $R^1$, $R^4$ and $R^{4'}$ are defined as above; and hydrolyzing the compound of the formula (X) to obtain the compound of the formula (IX)

(IX)

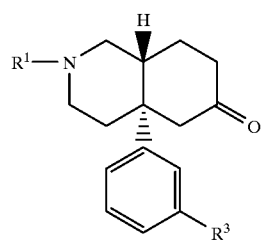

wherein $R^1$ is defined as above, and R3 is hydroxyl group.

3. The process for producing 4a-aryl-trans-6-oxodecahydroisoquinoline compounds according to claim 1 or 2, wherein the compound of the formula (II)

(II)

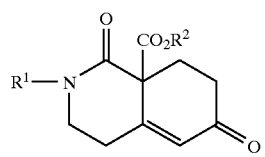

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, is reacted with an aromatic metal compound prepared from the compound of the formula (III)

(III)

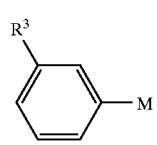

wherein $R^3$ is hydrogen atom, $C_1$–$C_4$ alkoxy or benzyloxy, M is lithium, magnesium chloride, magnesium bromide cr magnesium iodide, and a metal compound, the metal of which is trivalent aluminum, divalent manganese, divalent zinc or monovalent copper, to convert the compound of the formula (II) to the compound of the formula (IV)

(IV)

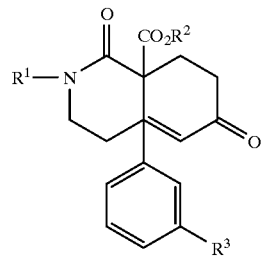

wherein $R^1$, $R^2$ and $R^3$ are defined as above.

4. The process for producing 4a-aryl-trans-6-oxodecahydroisoquinoline compounds according to claim 1 or 2, wherein the compound of formula (II)

(II)

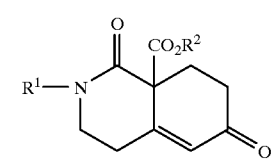

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, is reacted with an aromatic metal compound prepared from the compound of the formula (III)

(III)

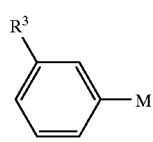

wherein $R^3$ is a hydrogen atom, $C_1$–$C_4$ alkoxy or benzyloxy, M is lithium, magnesium chloride, magnesium bromide or magnesium iodide, and a metal compound, the metal of which is divalent manganese or monovalent copper, to convert the compound of the formula (II) to the compound of formula (IV)

(IV)

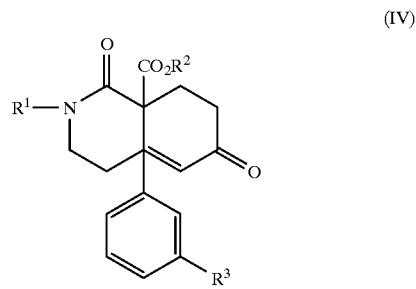

wherein $R^1$, $R^2$ and $R^3$ are defined as above.

5. The process for producing 4a-aryl-trans-6-oxodecahydroisoquinoline compounds according to claim 1 or 2, wherein the compound of the formula (I)

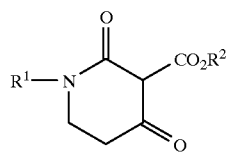
(I)

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, is reacted with methylvinylketone in the presence of an inorganic base or a metal alkoxide and a crown ether; in the presence of a corresponding metal alkoxide in an alcohol; or in the presence of an alkaline metal fluoride, to convert the compound of the formula (I) to the compound of the formula (II)

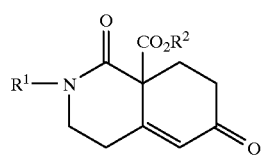
(II)

wherein $R^1$ and $R^2$ are defined as above.

6. The process for producing 4a-aryl-trans-6-oxodecahydroisoquinoline compounds according to claim 1 or 2, wherein the compound of the formula (VII)

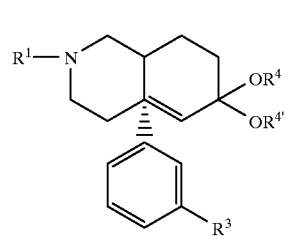
(VII)

wherein $R^1$ is $C_1$–$C_6$ alkyl, allyl, benzyl, phenethyl or $C_4$–$C_7$ cycloalkylalkyl, $R^3$ is a hydrogen atom, $C_1$–$C_4$ alkoxy or benzyloxy, $R^4$ and $R^{4'}$ independently are methyl or ethyl, or $R^4$ and $R^{4'}$ are bonded to form ethylene or trimethylene, is reduced with sodium cyanoborohydride in acidic conditions to a compound of the formula (VIII)

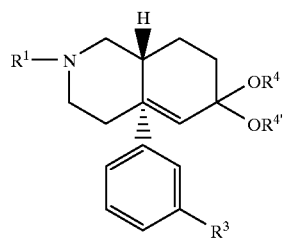
(VIII)

wherein $R^1$, $R^3$, $R^4$ and $R^{4'}$ are defined as above.

7. The process for producing 4a-aryl-trans-6-oxodecahydroisoquinoline compounds according to claim 1 or 2, wherein the compound of the formula (II)

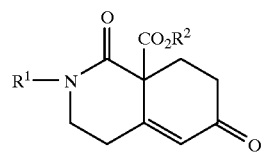
(II)

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, is reacted with an aromatic metal compound prepared from a compound of the formula (III)

(III)

$$\text{(structure with } R^3 \text{ and } M \text{)}$$

wherein $R^3$ is a hydrogen atom, $C_1$–$C_4$ alkoxy or benzyloxy, M is lithium, magnesium chloride, magnesium bromide or magnesium iodide, and a metal compound, the metal of which is selected from the group of metals belonging to Groups VIIB, VIII, IB, IIB, IIIA, to convert the compound (II) to a compound of the formula (IV)

(IV)

$$\text{(structure)}$$

wherein $R^1$, $R^2$ and $R^3$ are defined as above.

8. A method for making 4a-aryl-trans-6-oxodecahydroisoquinoline compounds comprising:

reacting a compound of the formula (II)

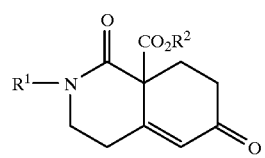
(II)

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, with an aromatic metal compound prepared from a compound of the formula (III)

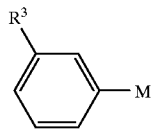
(III)

wherein $R^3$ is a hydrogen atom, $C_1$–$C_4$ alkoxy or benzyloxy, M is lithium, magnesium chloride, magnesium bromide or magnesium iodide, and a metal compound, the metal of which is selected from the group of metals belonging to Groups VIIIB, VIII, IB, IIB, IIIA, to convert the compound (II) to a compound of the formula (IV)

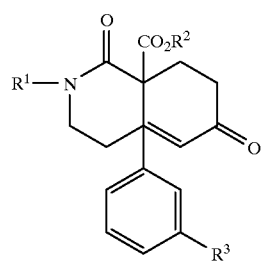
(IV)

wherein $R^1$, $R^2$ and $R^3$ are defined as above;

reacting the compound of the formula (IV) with an alcohol to convert the compound of the formula (IV) to a compound of the formula (V)

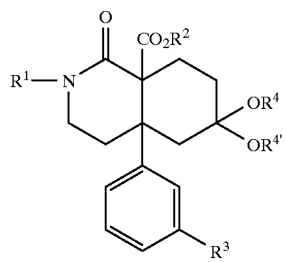
(V)

wherein $R^1$, $R^2$ and $R^3$ are defined as above, $R^4$ and $R^{4'}$ independently are methyl or ethyl, or $R^4$ and $R^{4'}$ are bonded to form ethylene or trimethylene;

decarboxylating the compound of the formula (V), to convert the compound of the formula (V) to a compound of the formula (VI)

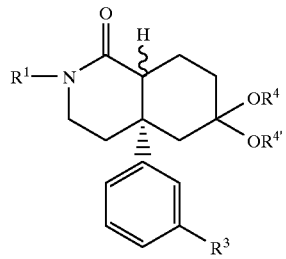
(VI)

wherein $R^1$, $R^3$, $R^4$ and $R^{4'}$ are defined as above.

9. A method for making 4a-aryl-trans-6-oxodecahydroisoquinoline compounds comprising:
reacting the compound of the formula (II)

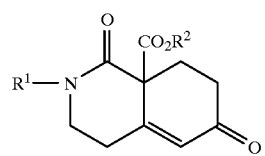
(II)

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, with an aromatic metal compound prepared from a compound of the formula (III)

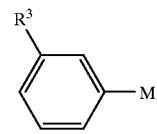
(III)

wherein $R^3$ is a hydrogen atom, $C_1$–$C_4$ alkoxy or benzyloxy, M is lithium, magnesium chloride, magnesium bromide cr magnesium iodide, and a metal compound, the metal of which is selected from the group of metals belonging to Groups VIIIB, VIII, IB, IIB, IIIA, to convert the compound (II) to a compound of the formula (IV)

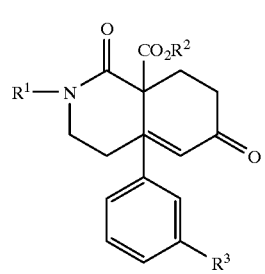
(IV)

wherein $R^1$, $R^2$ and $R^3$ are defined as above.

10. A method for making 4a-aryl-trans-6-oxodecahydroisoquinoline compounds comprising:

reacting a compound of the formula (II)

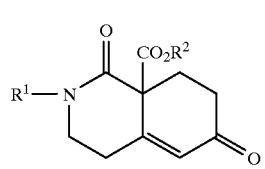

(II)

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, with an aromatic metal compound prepared from a compound of the formula (III)

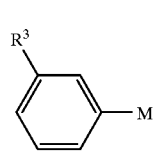

(III)

wherein $R^3$ is a hydrogen atom, $C_1$–$C_4$ alkoxy or benzyloxy, M is lithium, magnesium chloride, magnesium bromide or magnesium iodide, and a metal compound, the metal of which is trivalent aluminum, divalent manganese, divalent zinc or monovalernt copper to convert the compound of the formula (II) to the compound of the formula (IV)

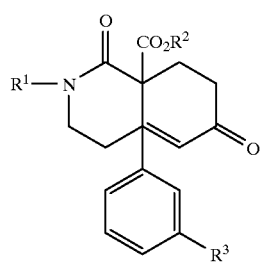

(IV)

wherein $R^1$, $R^2$ and $R^3$ are defined as above.

11. A method for making 4a-aryl-trans-6-oxodecahydroisoquinoline compounds comprising:

reacting a compound of the formula (II)

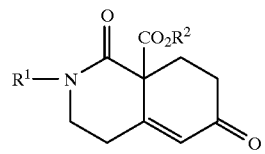

(II)

wherein $R^1$ is $C_1$–$C_6$ alkyl, allyl, benzyl, phenethyl or $C_4$–$C_7$ cycloalkylalkyl and $R^2$ is $C_1$–$C_4$ alkyl or benzyl, with an aromatic metal compound prepared from a compound of the formula (III)

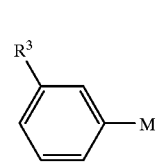

(III)

wherein $R^3$ is a hydrogen atom, $C_1$–$C_4$ alkoxy or benzyloxy, M is lithium, magnesium chloride, magnesium bromide or magnesium iodide, and a metal compound, the metal of which is divalent manganese or monovalent copper to convert the compound of the formula (II) to a compound of the formula (IV)

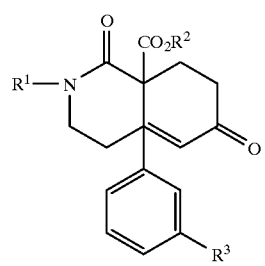

(IV)

wherein $R^1$, $R^2$ and $R^3$ are defined as above.

* * * * *